United States Patent
Stem et al.

(10) Patent No.: US 11,963,659 B2
(45) Date of Patent: Apr. 23, 2024

(54) ENDOSCOPE INCLUDING AN ELONGATE VIEWING INSTRUMENT WITH A PRE-BIASED DISTAL PORTION

(71) Applicant: GYRUS ACMI, INC., Westborough, MA (US)

(72) Inventors: Jessica N. Stem, Coon Rapids, MN (US); Connor Tower, Hudson, MA (US)

(73) Assignee: Gyrus ACMI, Inc., Westborough, MA (US)

(*) Notice: Subject to any disclaimer, the term of this patent is extended or adjusted under 35 U.S.C. 154(b) by 128 days.

(21) Appl. No.: 17/331,073

(22) Filed: May 26, 2021

(65) Prior Publication Data

US 2021/0369095 A1 Dec. 2, 2021

Related U.S. Application Data

(60) Provisional application No. 63/030,051, filed on May 26, 2020.

(51) Int. Cl.
*A61B 1/00* (2006.01)
*A61B 1/01* (2006.01)
(Continued)

(52) U.S. Cl.
CPC .... *A61B 1/00078* (2013.01); *A61B 1/000094* (2022.02); *A61B 1/00045* (2013.01);
(Continued)

(58) Field of Classification Search
None
See application file for complete search history.

(56) References Cited

U.S. PATENT DOCUMENTS 3,707,146 A * 12/1972 Cook ............... A61B 1/00082
604/920
4,660,573 A * 4/1987 Brumbach ....... A61B 17/22012
606/128

(Continued)

FOREIGN PATENT DOCUMENTS

CN 115697173 A 2/2023
WO WO-2021242853 A1 12/2021

OTHER PUBLICATIONS

"International Application Serial No. PCT/US2021/034238, International Preliminary Report on Patentability dated Dec. 8, 2022", 9 pgs.

(Continued)

*Primary Examiner* — John P Leubecker
(74) *Attorney, Agent, or Firm* — Schwegman Lundberg & Woessner, P.A.

(57) ABSTRACT

An endoscope can include a substantially rigid elongate body. A visualization channel can extend through the elongate body. An elongate viewing instrument that can advance distally and retract proximally through a visualization channel of the elongate body. The elongate viewing instrument can include a distal portion that is pre-biased to assume a curved shape when the distal portion is unconfined. The distal portion can curve when the distal portion is advanced distally to exit the visualization channel and can straighten when the distal portion is retracted proximally to enter the visualization channel. A distal end of the elongate viewing instrument can further include a light port that is configured to illuminate a target and provide an image of the illuminated target.

19 Claims, 14 Drawing Sheets

(51) Int. Cl.
*A61B 1/018* (2006.01)
*A61B 1/06* (2006.01)
*A61B 18/26* (2006.01)
*A61B 18/00* (2006.01)

(52) U.S. Cl.
CPC ............ *A61B 1/00126* (2013.01); *A61B 1/01* (2013.01); *A61B 1/018* (2013.01); *A61B 18/26* (2013.01); *A61B 1/06* (2013.01); *A61B 2018/00511* (2013.01); *A61B 2018/00577* (2013.01); *A61B 2218/002* (2013.01)

(56) References Cited

U.S. PATENT DOCUMENTS

| | | | | |
|---|---|---|---|---|
| 4,932,954 | A * | 6/1990 | Wondrazek | A61B 18/26 606/2.5 |
| 4,968,314 | A * | 11/1990 | Michaels | A61B 18/26 606/7 |
| 4,991,957 | A * | 2/1991 | Sakamoto | A61B 1/009 356/241.4 |
| 5,009,658 | A * | 4/1991 | Damgaard-Iversen | H01S 3/11 606/2.5 |
| 5,059,200 | A * | 10/1991 | Tulip | A61B 18/26 606/2.5 |
| 5,188,111 | A * | 2/1993 | Yates | G01R 33/285 128/DIG. 7 |
| 5,242,454 | A * | 9/1993 | Gundlach | A61B 18/26 606/127 |
| 5,496,306 | A * | 3/1996 | Engelhardt | A61B 18/26 606/2.5 |
| 5,728,148 | A * | 3/1998 | Bostrom | A61N 1/056 607/116 |
| 5,733,503 | A * | 3/1998 | Kowatsch | A61L 2/26 422/294 |
| 5,810,715 | A * | 9/1998 | Moriyama | A61B 1/0051 600/141 |
| 5,860,972 | A * | 1/1999 | Hoang | A61B 18/26 606/127 |
| 6,264,664 | B1 * | 7/2001 | Avellanet | A61B 17/221 606/1 |
| 9,345,387 | B2 * | 5/2016 | Larkin | A61B 34/70 |
| 2002/0013550 | A1 * | 1/2002 | Unsworth | A61B 1/0058 604/113 |
| 2004/0019359 | A1 * | 1/2004 | Worley | A61M 25/0041 600/585 |
| 2004/0054257 | A1 * | 3/2004 | Brown | A61B 1/0058 600/151 |
| 2004/0133075 | A1 * | 7/2004 | Motoki | A61B 1/00147 600/153 |
| 2005/0020901 | A1 * | 1/2005 | Belson | G02B 23/2476 600/407 |
| 2005/0119527 | A1 * | 6/2005 | Banik | A61B 1/0055 600/117 |
| 2005/0272975 | A1 * | 12/2005 | McWeeney | A61M 25/0068 600/172 |
| 2006/0189844 | A1 * | 8/2006 | Tien | A61B 1/01 600/146 |
| 2006/0252993 | A1 * | 11/2006 | Freed | A61B 1/0052 604/95.04 |
| 2007/0177008 | A1 * | 8/2007 | Bayer | A61B 1/00096 348/65 |
| 2007/0270640 | A1 * | 11/2007 | Dimitriou | A61B 1/00128 600/106 |
| 2008/0021274 | A1 * | 1/2008 | Bayer | A61B 1/00101 600/117 |
| 2008/0058595 | A1 | 3/2008 | Snoke et al. | |
| 2009/0143645 | A1 * | 6/2009 | Matthes | A61B 1/0125 600/120 |
| 2009/0299352 | A1 * | 12/2009 | Zerfas | A61B 1/0051 606/15 |
| 2011/0106055 | A1 * | 5/2011 | Robertson | A61B 1/0051 604/525 |
| 2012/0162401 | A1 * | 6/2012 | Melder | H04N 7/183 348/E7.085 |
| 2012/0289783 | A1 * | 11/2012 | Duindam | A61B 90/03 600/118 |
| 2013/0060084 | A1 * | 3/2013 | Fouts | A61B 17/3421 600/106 |
| 2013/0184528 | A1 * | 7/2013 | Onuki | A61B 17/062 600/146 |
| 2013/0237968 | A1 * | 9/2013 | Schaeffer | A61B 17/3421 606/127 |
| 2014/0213848 | A1 * | 7/2014 | Moskowitz | A61B 17/29 600/106 |
| 2014/0213849 | A1 | 7/2014 | Pandey | |
| 2015/0057537 | A1 * | 2/2015 | Dillon | A61B 1/0014 600/113 |
| 2016/0128773 | A1 * | 5/2016 | Ogawa | A61B 17/2909 606/205 |
| 2016/0166129 | A1 * | 6/2016 | Walish | A61B 1/0052 600/104 |
| 2017/0188793 | A1 * | 7/2017 | Ouyang | A61B 1/015 |
| 2018/0092701 | A1 * | 4/2018 | Fenech | A61B 34/71 |
| 2018/0206863 | A1 * | 7/2018 | Chu | A61B 1/00066 |
| 2018/0263705 | A1 * | 9/2018 | Jurevicius | A61B 1/00066 |
| 2019/0232027 | A1 * | 8/2019 | Chu | A61B 1/00133 |

OTHER PUBLICATIONS

"International Application Serial No. PCT US2021 034238, International Search Report dated Sep. 9, 2021", 4 pgs.
"International Application Serial No. PCT US2021 034238, Written Opinion dated Sep. 9, 2021", 7 pgs.

* cited by examiner

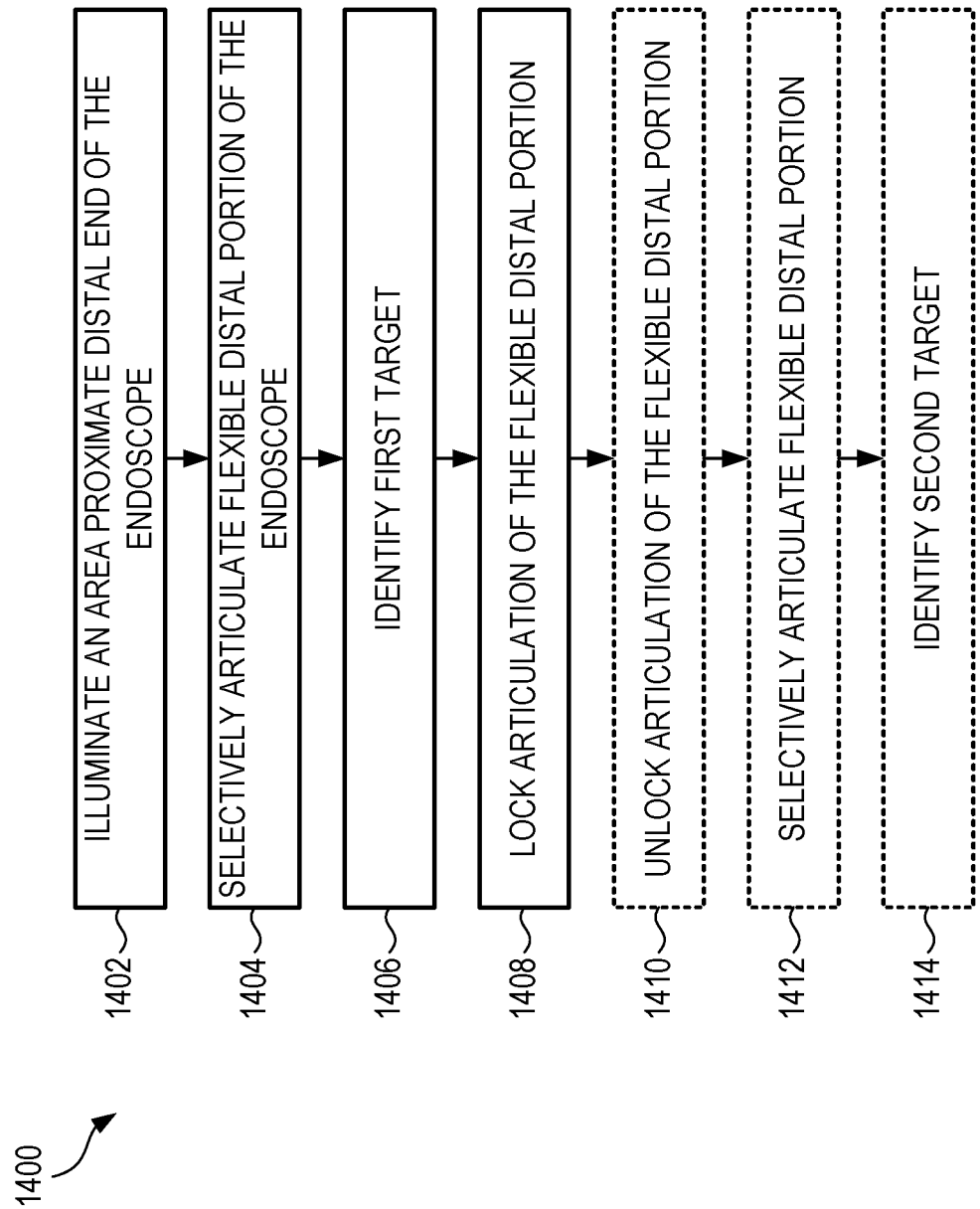

ENDOSCOPE INCLUDING AN ELONGATE VIEWING INSTRUMENT WITH A PRE-BIASED DISTAL PORTION

CROSS-REFERENCE TO RELATED APPLICATION

This application claims the benefit of U.S. Provisional Application No. 63/030,051, filed May 26, 2020, which is incorporated by reference herein in its entirety.

FIELD OF THE DISCLOSURE

The present disclosure relates generally to a device associated with a medical procedure to remove kidney stones.

BACKGROUND OF THE DISCLOSURE

A medical procedure referred to as percutaneous nephrolithotomy (PCNL) can be used to remove kidney stones, particularly stones that are relatively large, firm, resistant to other forms of stone treatment, or any combination thereof. A nephroscope is a viewing device, such as for viewing a kidney stone or other object within a region of a kidney.

SUMMARY

In an example, an endoscope can include a substantially rigid elongate body at least partially insertable into a kidney of a patient. The elongate body can include a visualization channel that extends through the elongate body from a proximal end of the elongate body to a distal end of the elongate body. An elongate viewing instrument can advance distally and retract proximally through the visualization channel of the elongate body. The elongate viewing instrument can extend distally beyond the distal end of the elongate body when the elongate viewing instrument is fully advanced distally. The elongate viewing instrument can include a distal portion that is pre-biased to assume a curved shape when the distal portion is unconfined, such that the distal portion of the elongate viewing instrument can curve when the distal portion of the elongate viewing instrument is advanced distally to exit the visualization channel and can generally straighten when the distal portion of the elongate viewing instrument is retracted proximally to enter the visualization channel. A distal end of the elongate viewing instrument can further include a light port that is configured to illuminate a target and provide an image of the illuminated target.

In an example, a method for adjusting an endoscope can include adjusting a relative spacing between an elongate body and a moveable actuator. The moveable actuator can include an elongate viewing instrument that extends distally from the moveable actuator. The elongate viewing instrument can extend through a visualization channel in the elongate body and can extend distally beyond a distal end of the elongate body such that adjusting the relative spacing adjusts how much of the elongate viewing instrument extends distally beyond the distal end of the elongate body. The elongate viewing instrument can include a distal portion that is pre-biased to assume a curved shape when the distal portion is unconfined, such that the distal portion of the elongate viewing instrument can curve when the distal portion of the elongate viewing instrument is advanced distally to exit the visualization channel and can generally straighten when the distal portion of the elongate viewing instrument is retracted proximally to enter the visualization channel. The method can further include automatically forcing, using one or more positioning elements on the elongate body that engage one or more corresponding positioning elements on the moveable actuator, the relative spacing to equal one of a plurality of specified spacings.

In an example, an endoscope can include an elongate body. A moveable actuator can be coupled to the elongate body. The moveable actuator can be moveable to adjust a relative spacing between the moveable actuator and the elongate body. An elongate viewing instrument can extend distally from the moveable actuator. The elongate viewing instrument can extend through a visualization channel in the elongate body and can extend distally beyond a distal end of the elongate body such that adjusting the relative spacing adjusts how much of the elongate viewing instrument extends distally beyond the distal end of the elongate body. The elongate viewing instrument can include a distal portion that is pre-biased to assume a curved shape when the distal portion is unconfined such that the distal portion of the elongate viewing instrument can curve when the distal portion of the elongate viewing instrument is advanced distally to exit the visualization channel and can generally straighten when the distal portion of the elongate viewing instrument is retracted proximally to enter the visualization channel. Positioning elements on the elongate body and the moveable actuator can snap the relative spacing between the moveable actuator and the elongate body to equal one of a plurality of specified spacings.

BRIEF DESCRIPTION OF THE DRAWINGS

FIG. 14 shows an example of a method for imaging using an endoscope.

Corresponding reference characters indicate corresponding parts throughout the several views. Elements in the drawings are not necessarily drawn to scale. The configurations shown in the drawings are merely examples and should not be construed as limiting in any manner.

DETAILED DESCRIPTION

Figure 1:
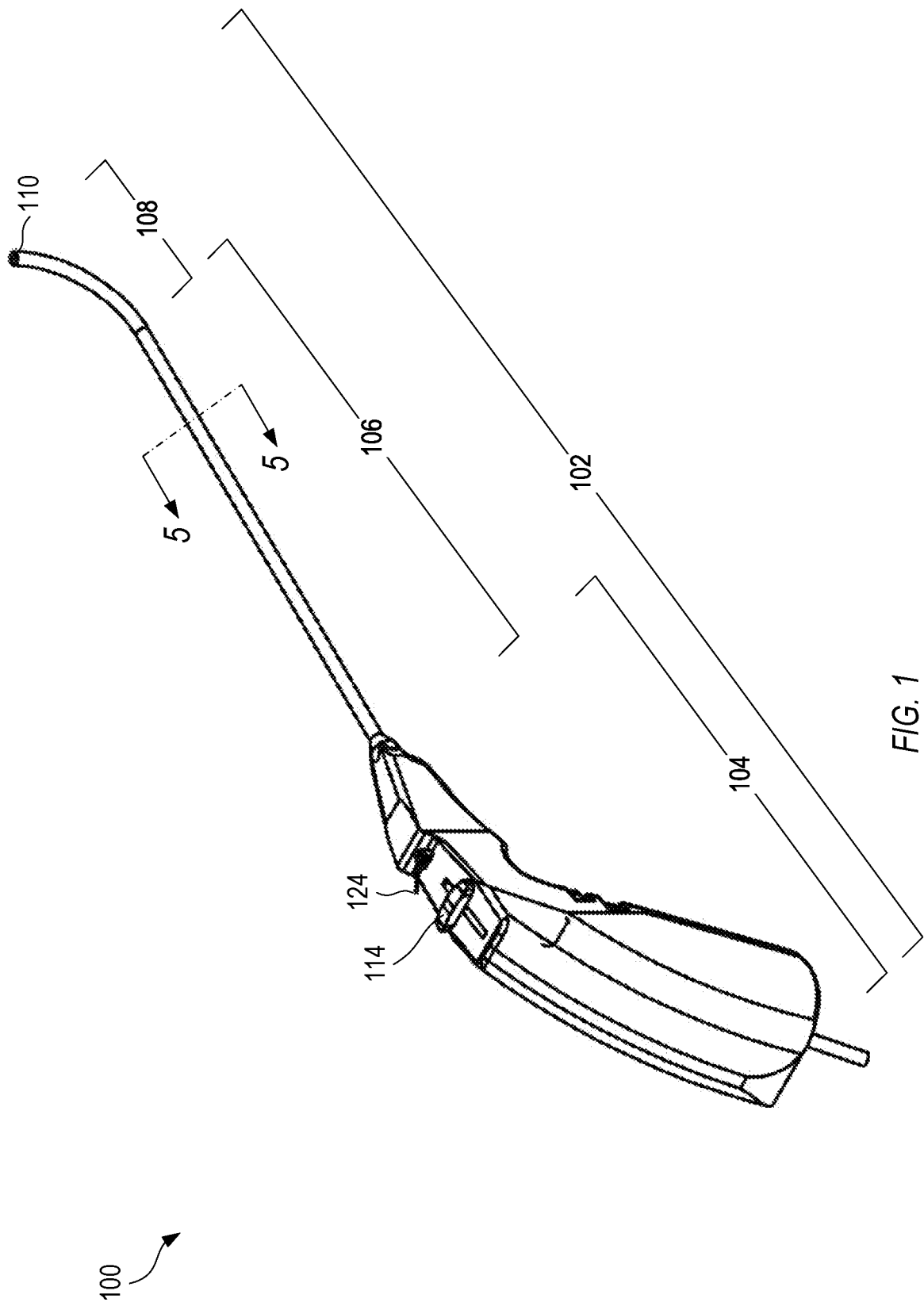
FIG. 1 shows a perspective view of an example of a nephroscope having a flexible distal portion.

The medical procedure referred to as percutaneous nephrolithotomy (PCNL) can be used to remove kidney stones, particularly stones that are relatively large, firm, resistant to other forms of stone treatment, or any combination thereof. In PCNL, a practitioner can insert a rigid endoscope through an incision in a patient's back and into the patient's kidney. Through the endoscope, the practitioner can locate the kidney stones, break the kidney stones into smaller fragments, and withdraw the stone fragments from the kidney. The endoscope can include an endoscope, a nephroscope, and/or a cystoscope.

In some procedures, the practitioner can break the stone into smaller fragments by applying a mechanical force, such as an oscillating force, to the stone, such as by applying a pulse with variable amplitudes and/or frequencies that originates outside the patient's body or using an ultrasonic lithotripter to apply an oscillating force. Once the stones have been broken into relatively small fragments, the practitioner can extract the small fragments through the endoscope.

Additionally or alternatively, the practitioner can break the stones into smaller fragments by illuminating the stone, through the endoscope, with relatively high-powered infrared laser light. The laser light can ablate a kidney stone into smaller fragments.

In some procedures, the practitioner may use one instrument for breaking the stone into smaller fragments and another, separate, instrument for visually examining other areas of the kidney. For example, a practitioner can use a rigid nephroscope to deliver the oscillating (or pulsatile) force. The rigid nephroscope can have limited viewing capabilities, so that the practitioner can see a relatively small area near a location of the oscillating force but cannot see anything located away from the small area. To view other portions of the kidney, the practitioner can withdraw the rigid nephroscope, and then use a flexible cystoscope to visually examine other areas of the kidney, such as to help ensure that the practitioner has accounted for and removed all of the fragments of the kidney stone. If the practitioner did miss a piece of the stone, the practitioner can then withdraw the flexible cystoscope, reinsert the rigid nephroscope to retrieve the missed piece of the stone, and reinsert the flexible cystoscope to repeat the visual examination of the other areas of the kidney.

There are drawbacks to using multiple instruments in such procedures. For example, it is time-consuming to repeatedly withdraw one instrument and insert another. In addition, it is relatively expensive to sterilize the flexible cystoscope for later surgeries.

As an improvement over such procedures, which use one instrument to break the stone into smaller fragments and another instrument to investigate other areas of the kidney, the nephroscope described herein can combine the functions of these two separate instruments into a single device. In addition to saving the practitioner time that would otherwise be spent swapping instruments, the nephroscope described herein can be configured for single use, which can reduce costs associated with sterilizing a reusable flexible cystoscope.

In addition, the nephroscope described herein can include elements that are movable with respect to one another to change the flexibility of the endoscope, such that the nephroscope can function as a flexible endoscope, can function as a rigid endoscope, and/or can switch between a flexible endoscope and a rigid endoscope. For example, such variable flexibility is described in detail below, with regard to FIGS. 8-10.

Figure 2:
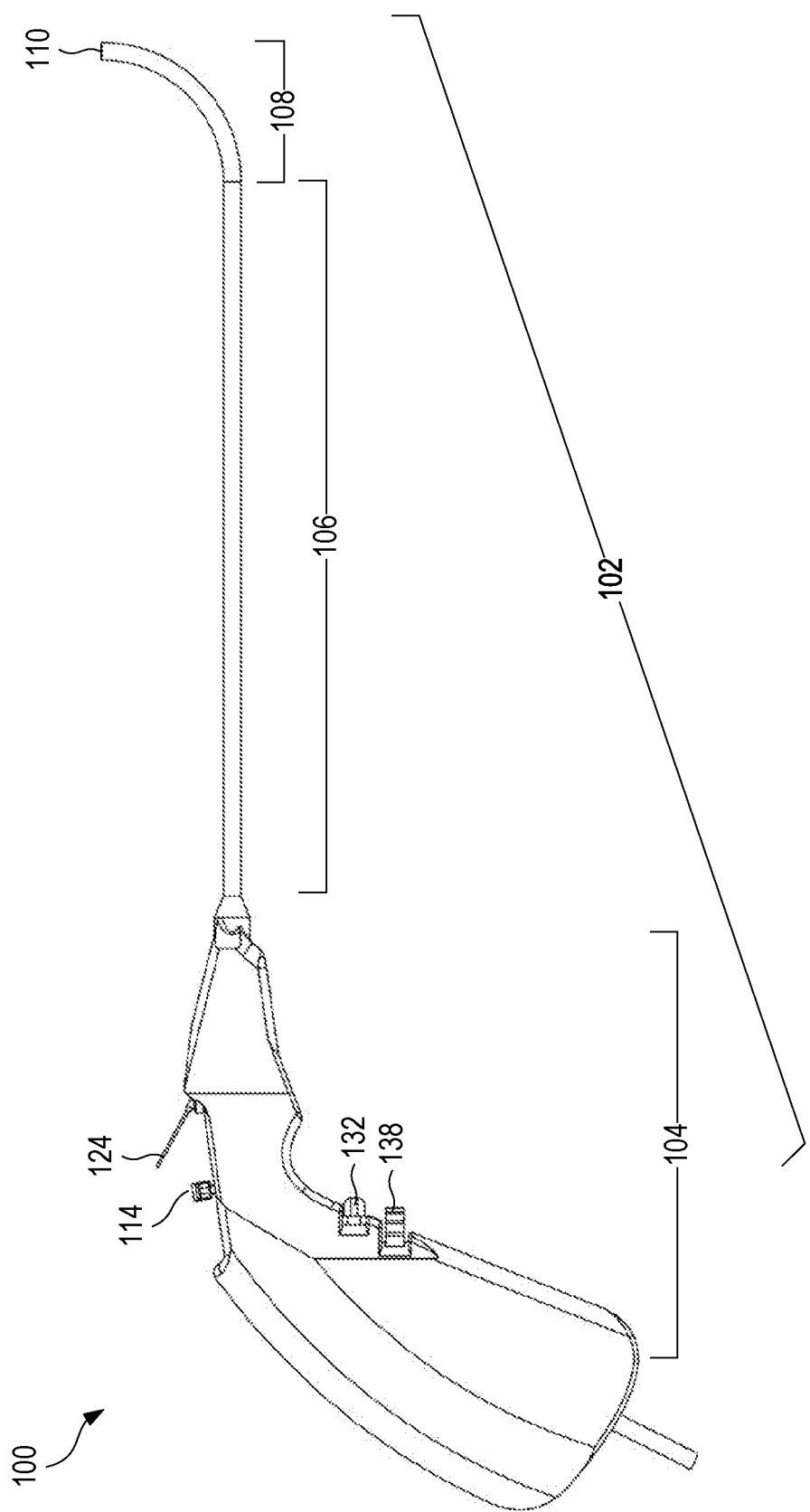
FIG. 2 shows a side view of the nephroscope of FIG. 1.
Figure 3:
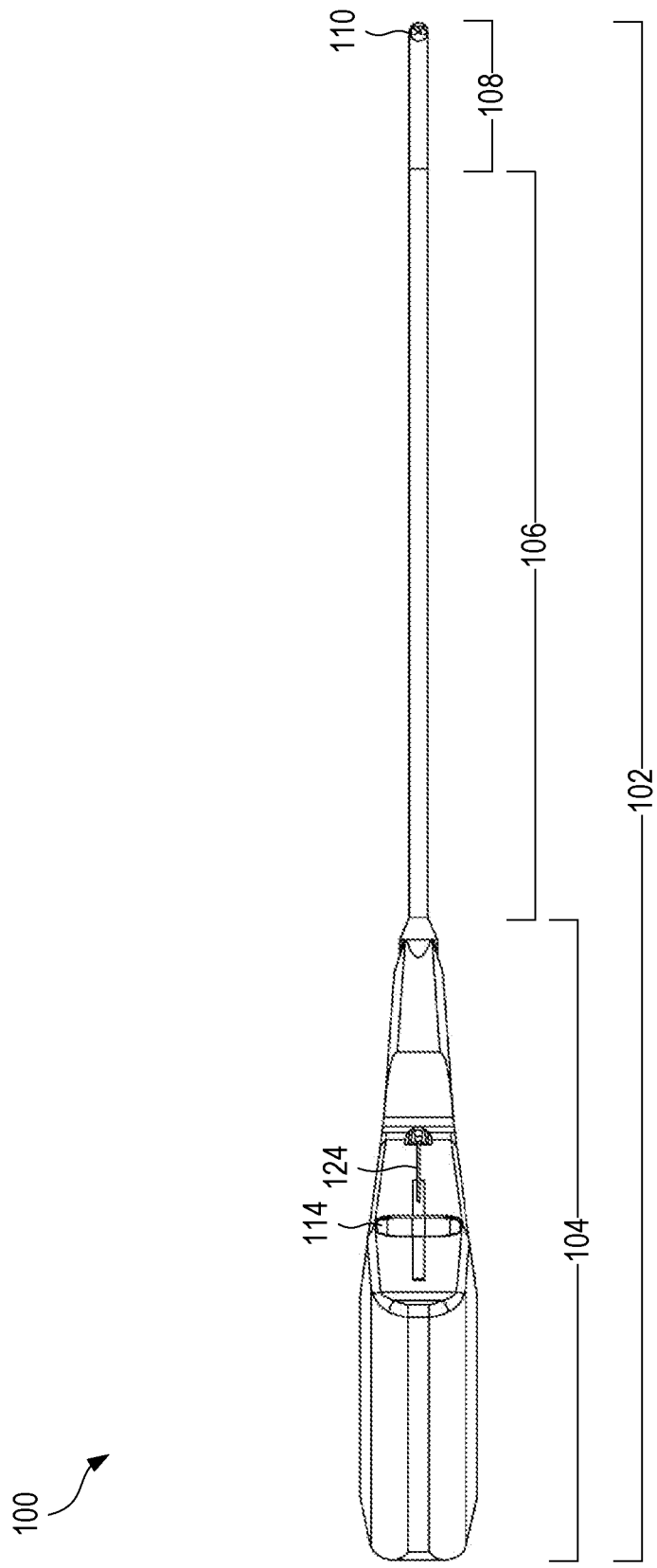
FIG. 3 shows a top view of the nephroscope of FIG. 1.
Figure 4:
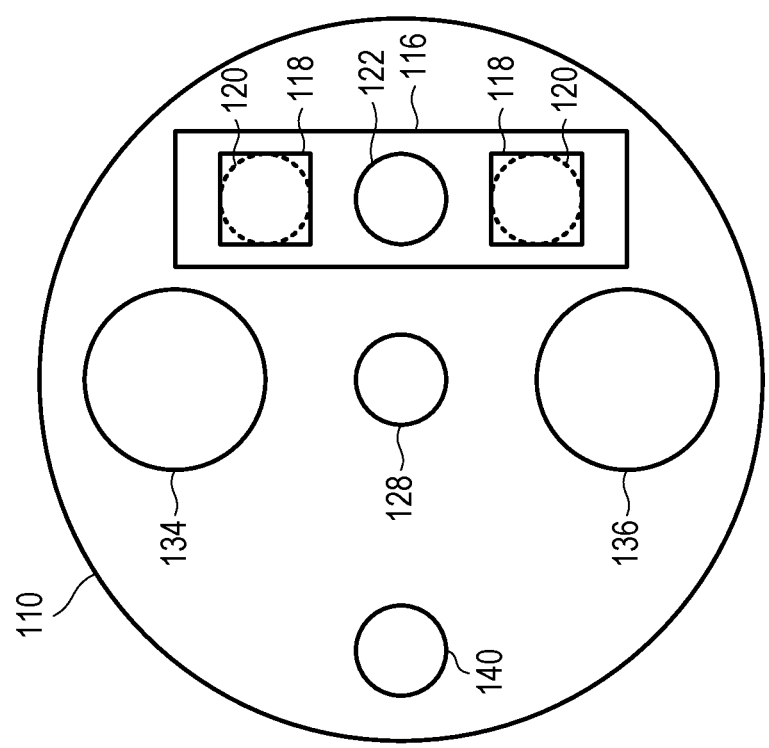
FIG. 4 shows an end-on view of the distal tip of the nephroscope of FIG. 1.
Figure 5:
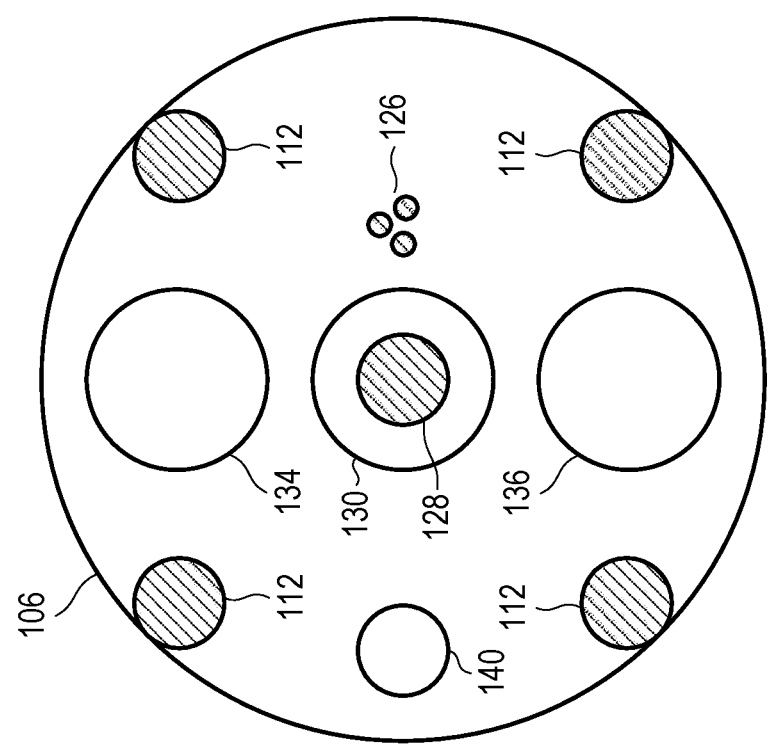
FIG. 5 shows a cross-sectional view of the elongated rigid portion of the nephroscope of FIG. 1.

FIG. 1 shows a perspective view of an example of a nephroscope 100 having a flexible distal portion. FIG. 2 shows a side view of the nephroscope 100 of FIG. 1. FIG. 3 shows a top view of the nephroscope 100 of FIG. 1. FIG. 4 shows an end-on view of the distal tip of the nephroscope 100 of FIG. 1. FIG. 5 shows a cross-sectional view of the elongated rigid portion of the nephroscope 100 of FIG. 1. The nephroscope 100 of FIGS. 1-5 is but one example of a nephroscope 100; other suitable configurations can also be used.

The nephroscope 100 can include a body 102 that is at least partially insertable into a kidney of a patient. The body 102 can include a handle, a hub, or other grippable proximal portion 104. The grippable proximal portion 104 can be formed from plastic, metal, or any other suitable material.

The body 102 can include an elongated rigid portion 106 extending from the grippable proximal portion 104. The elongated rigid portion 106 can be formed from plastic, metal, and/or any other suitable material. For example, the elongated rigid portion 106 can include a polymer outer portion that surrounds a stainless-steel wire mesh, which in turn surrounds additional components of the nephroscope 100 that are described in detail below. The elongated rigid portion 106 can remain rigid, relative to the grippable proximal portion 104, when the practitioner inserts the nephroscope 100 into the body of the patient, and when the practitioner passes one or more stone-fragmenting instruments, such as an ultrasonic lithotripter, through the nephroscope 100.

The body 102 can include a flexible distal portion 108 extending distally from the elongated rigid portion 106 to a distal end 110. The flexible distal portion 108 can be more flexible than the elongated rigid portion 106. For example, the flexible distal portion 108 can include a series of rigid rings, each ring connected to the adjacent rings by a respective joint that includes a pivot pin, each pivot pin being circumferentially offset from an adjacent pin by 90 degrees. The pins and rings can form a manipulatable structure that can curl in any direction.

One or more pull wires 112 (see FIG. 5) can extend along the body 102 to the flexible distal portion 108. The pull wires 112 can control the curl of the flexible distal portion 108. The pull wires 112 can be located at a respective plurality of angular locations on the body 102 and on the flexible distal portion 108. For examples in which the body 102 has one or more portions that have a circular cross-section, the angular locations can correspond to circumferential locations around the circular cross-section of the body 102. As a specific example in FIG. 5, there are four pull wires 112 positioned at angular locations of 45 degrees, 135 degrees, 225 degrees, and 315 degrees, with respect to a horizontal axis (or a vertical axis) in FIG. 5. Other numbers of pull wires and other angular locations can also be used.

An articulation controller 114 can be located on the grippable proximal portion 104 of the body 102. The articulation controller 114 can be located to be actuatable by a thumb of the human hand when the human hand grips the grippable proximal portion 104 of the body 102. The articulation controller 114 can adjust the position of the flexible distal portion 108. The articulation controller 114 can adjust the position by controllably applying a proximally oriented force to a first pull wire 112, where the first pull wire 112 is located at a first angular location. The proximally oriented force can cause the flexible distal portion 108 of the body 102 to move radially in the direction of the first angular location. The pull wires 112 and the articulation controller 114 can adjust a position of the flexible distal portion 108 to locate a kidney stone when the body 102 is inserted into the kidney of the patient.

In a specific example, the nephroscope 100 can include four pull wires 112 positioned at angular locations of 45 degrees, 135 degrees, 225 degrees, and 315 degrees, with respect to a horizontal axis (or a vertical axis) in FIG. 5. In this specific example, the pull wires 112 at 45 degrees and 225 degrees are joined together around a first gear in the grippable proximal portion 104, and the pull wires 112 at 135 degrees and 315 degrees are joined together around a second gear in the grippable proximal portion 104. In this specific example, the articulation controller 114 can include a first knob coupled to the first gear, which can controllably pull on one of the pull wires 112 at 45 degrees and 225 degrees and push on the other of the pull wires 112 at 45 degrees and 225 degrees. Similarly, the articulation controller 114 can include a second knob coupled to the second gear, which can controllably pull on one of the pull wires 112 at 135 degrees and 315 degrees and push on the other of the pull wires 112 at 135 degrees and 315 degrees.

Once a practitioner has located a stone, the practitioner can use the articulation controller 114, or another suitable element, to lock the articulation of the flexible distal portion 108. For example, the articulation controller 114, or other suitable element, can removably force the pull wires 112 against one or more fixed elements in the grippable proximal portion 104 of the body 102, thereby locking the pull wires 112 in place, and in turn locking a position of the flexible distal portion 108. Other suitable locking mechanisms can also be used, including the configuration shown in FIGS. 8-10 and discussed below. The articular controller 114 can deploy the locking mechanism via a button, a lever, a slider, a switch, a dial, or another suitable deployment mechanism. With the articulation being locked, the practitioner can deploy a lithotripter as needed. This locking of the articulation of the flexible distal portion 108 can be referred to as the flexible distal portion 108 being selectively flexible.

The articulation controller 114, or other suitable element, can also unlock the articulation of the flexible distal portion 108. For example, the articulation controller 114, or other suitable element, can release the pull wires 112 from the one or more fixed elements in the grippable proximal portion 104 of the body 102. The articular controller 114 can use the locking mechanism to deploy the unlocking mechanism. For example, the locking mechanism can involve depressing a button, and the unlocking mechanism can involve releasing or pulling the button. The articular controller can 114 can use a separate button, lever, slider, switch, dial, or another suitable deployment mechanism to unlock the articulation of the flexible distal portion 108. With the articulation being unlocked, the practitioner can reposition the flexible distal portion 108 as needed to inspect additional portions of the kidney. Other locking and/or unlocking mechanisms can also be used. The articular controller 114 can switch between a first configuration, in which the position of the flexible distal portion 108 is adjustable, and a second configuration, in which the position of the flexible distal portion 108 is lockable at a selectable position. This is but one example of a configuration for the pull wires 112 and the articulation controller 114; other configurations can also be used.

The flexible distal portion 108 can be flexible relative to the handle or the elongated rigid portion 106 once inside the kidney and during imaging. The flexible distal portion 108 can have sufficient columnar strength to ensure that it can be inserted through the puncture. The flexible distal portion 108 can be constructed similar to flexible endoscopes. The flexible distal portion 108 can include a torque carrier and additional supporting structures, such as a braid or a mesh, that can help provide columnar strength and can help increase pushability but may still be flexible relative to the elongated rigid portion 106. The articulation controller 114 can control the articulation of the flexible distal portion 108 so that the flexible distal portion 108 can be rigid (with a comparable rigidity to the elongated rigid portion 106) during insertion through the puncture into the kidney, and may be actuated to adjust the rigidity so that the flexible distal portion 108 can be distally moved and imaged once inside the kidney. Once the stone is located, the articulation controller 114 can be actuated again so that flexible distal portion 108 can have sufficient rigidity and its articulation is locked. The flexible distal portion 108 can therefore be stationary relative to the elongated rigid portion 106 and not move any further, during stone ablation. After ablation, the practitioner can further articulate the flexible distal portion 108 to do further imaging.

A substrate 116 (see FIG. 4) can be located on the distal end 110 of the body 102. The substrate 116 can include one or more of a circuit board, a hybrid chip, a ceramic component, or other suitable components or elements. The substrate 116, and any components located on the substrate 116, can be formed separately from the body 102 and can be subsequently attached to the distal end 110 of the body 102. The substrate 116, and any components located on the substrate 116, can be formed integrally with the distal end 110 of the body 102. The substrate 116 can be formed integrally with the distal end 110 of the body 102, and any components located on the substrate 116 can be subsequently attached to the substrate 116.

To visualize the kidney stone fragments, the nephroscope 100 can include a visualization system at the distal end 110 of the body 102. The visualization system can illuminate a working area of the kidney stone and can generate a video image or one or more static images of the illuminated area of the kidney stone.

Figure 6:
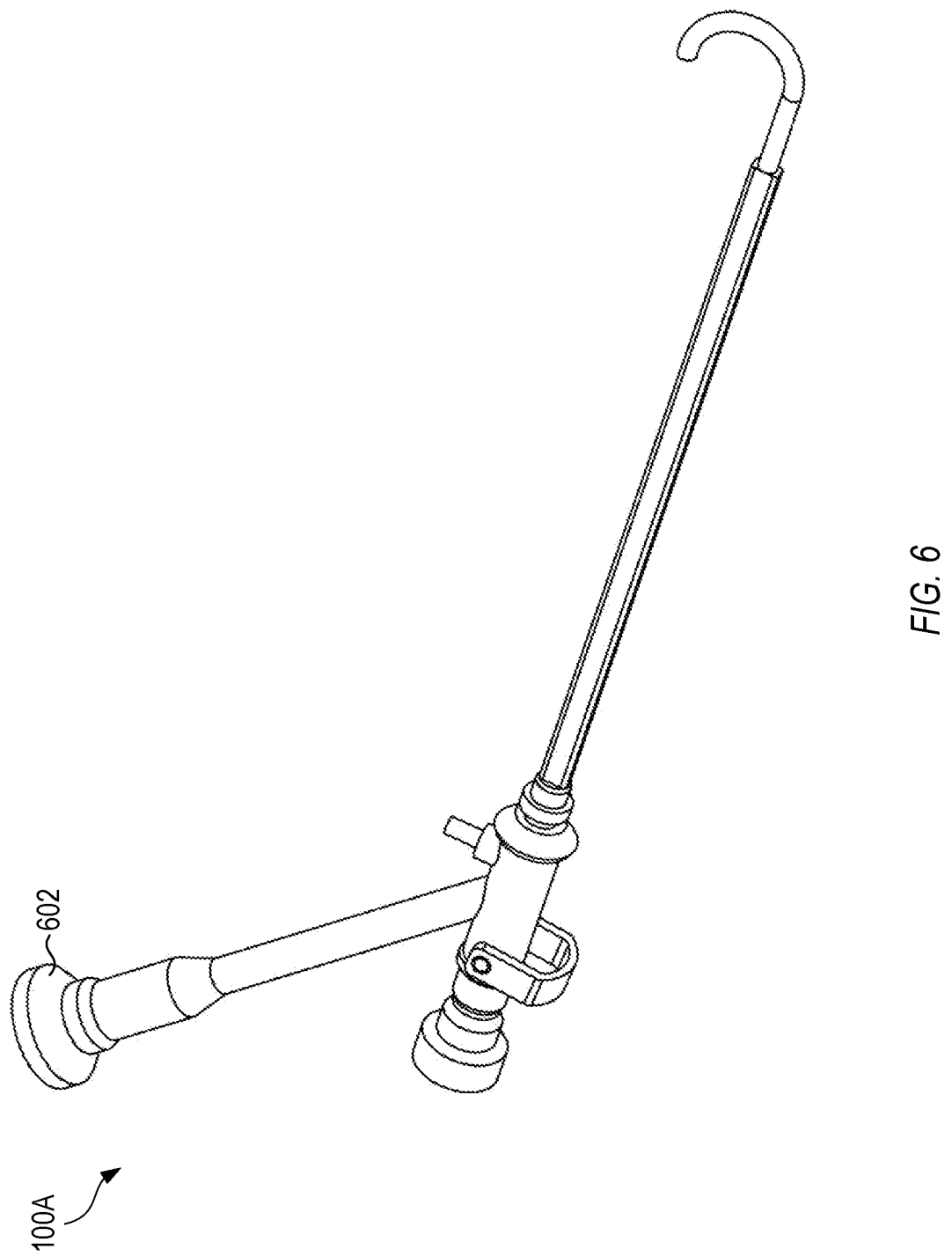
FIG. 6 shows a perspective view of an example of a nephroscope having a flexible distal portion and having a video monitor that is attached to or formed integrally with the nephroscope.

FIG. 6 shows a perspective view of an example of a nephroscope 100A having a flexible distal portion and having a video monitor 602 that is attached to or formed integrally with the nephroscope 100A. The visualization system can direct the video image to a display, such as the video monitor 602. The display can be external to the nephroscope 100 and can be viewable during the kidney stone removal procedure. The video monitor 602 can be used with any or all of the elements of the nephroscope 100 of FIGS. 1-5.

Returning to FIGS. 1-5, the visualization system can include at least one light-emitting diode 118 (see FIG. 4) located on the substrate 116. The substrate 116 can be a circuit board that mechanically supports and electrically powers each light-emitting diode 118. The light-emitting diode or diodes 118 can emit light distally away from the distal end 110 of the body 102 to illuminate the kidney stone. One or more light-emitting diodes 118 can emit white light to illuminate the kidney stone. White light can allow the practitioner to observe discolorations or other color-based effects on the kidney stones or on the tissue proximate the distal end 110 of the body 102. One or more light-emitting diodes 118 can emit blue light to illuminate the kidney stone. Blue light can be well-suited to show thermal tissue spread and thereby detect damage in the tissue. Other colors and/or color bands, such as red, amber, yellow, green, or others, can also be used.

The substrate 116 can include an optional lens 120 (see FIG. 4) for each light-emitting diode 118, which can angularly adjust the light output from the light-emitting diode 118. The lens 120 can narrow the light output from the light-emitting diode 118. The lens 120 can widen the light output from the light-emitting diode 118. Such an angular adjustment can help ensure that the kidney stones and the tissue are sufficiently illuminated within a specified angular field of view.

The visualization system can include a camera 122 (see FIG. 4) located on the substrate 116. The substrate 116 can be a circuit board that mechanically supports and electrically powers the camera 122. The camera 122 can capture a video image or one or more static images of the illuminated kidney stone. The video image can be in real-time, or nearly real-time with a relatively short latency for processing, so that the practitioner can observe the kidney stone and the surrounding tissue as the practitioner manipulates the body 102 and controls of the nephroscope 100. The camera 122 can include a lens and a multi-pixel sensor located at a focal plane of the lens. The sensor can be a color sensor, such as a sensor that provides intensity values for red light, green light, and blue light for each pixel in the video image. The circuit board can produce a digital video signal representing the captured video image of the illuminated kidney stone. The digital video signal can have a video refresh rate of 10 Hz, 20 Hz, 24 Hz, 25 Hz, 30 Hz, 40 Hz, 50 Hz, 60 Hz, or another suitable video refresh rate.

The at least one light-emitting diode 118 can include two light-emitting diodes 118. The camera 122 can be located between the two light-emitting diodes 118. The at least one light-emitting diode 118 can include multiple light-emitting diodes 118 that surround the camera 122. Each of the multiple light-emitting diodes 118 can emit the same color band or different color bands. For example, one light-emitting diode of the multiple light emitting diodes 118 can emit white light and another can emit blue light. The different light sources can be used to better visualize different elements within the body, such as a kidney stone or tissue, as described above. These orientations of the light-emitting diodes 118 and the camera 122 can be beneficial in that the illumination can be relatively uniform over the field of view of the camera 122 (e.g., the illumination may have relatively little bias toward one side of the field of view).

The visualization system can include an electrical port 124 on the body 102 and coupled to the substrate 116, such as the circuit board. For example, one or more wires 126 can extend along the body 102 from the electrical port 124 to the substrate 116. The electrical port 124 can receive electrical power to power the circuit board. The electrical port 124 can provide a wired connection to the digital video signal via a suitable, optionally multi-pin, electrical connector. The substrate 116, such as the circuit board, can communicate the digital video signal wirelessly to a display device that is external to the nephroscope 100, such as a user device, a display, a computer monitor, a heads-up display, a wearable display, a virtual reality display, an augmented reality display, and others. The electrical port 124 can include one or more seals that can help prevent irrigation fluid, which can be pressurized, from passing through the electrical port 124 and potentially damaging one or more components and/or leaking out of the device. One or more seals can surround one or more wires and/or electrical connectors. One or more seals can be located at a proximal end of the electrical port 124 and/or a distal end of the electrical port 124.

An optical fiber 128 (see FIG. 5) can extend along a working channel 130 (see FIG. 5) in the body 102 to the distal end 110 of the body 102. The optical fiber 128 can deliver laser light to the kidney stone to ablate the kidney stone into kidney stone fragments.

The optical fiber 128 can be integrated into the nephroscope 100. For example, the optical fiber 128 can be shipped with the nephroscope 100, and/or can remain with the nephroscope 100 after use. The optical fiber 128 can be separate from the nephroscope 100. For example, the optical fiber 128 can be fed along a working channel of the nephroscope 100 prior to use, and/or retrieved from a working channel of the nephroscope 100 after use.

A laser or laser emitter, external to the nephroscope 100, can generate the laser light. The laser light can be coupled into a proximal end of the optical fiber 128 via a suitable connector. The laser light can have a wavelength that corresponds to a spectral peak of absorption of human blood and saline, such as 2100 nm, 1942 nm, and others. For example, wavelengths in the range between 1900 nm and 3000 nm can correspond to a spectral region in which water is absorbing, while wavelengths between 400 nm and 520 nm can correspond to a spectral region in which oxy-hemoglobin and/or deoxy-hemoglobin is absorbing. For example, a thulium fiber laser can produce laser light at a wavelength of 1908 nm or 1940 nm, a thulium:YAG laser can produce laser light at a wavelength of 2010 nm, a holmium:YAG laser can produce laser light at a wavelength of 2120 nm, and an erbium:YAG laser can produce laser light at a wavelength of 2940 nm. Other wavelengths in these ranges can also be used. In general, delivering laser light that has significant absorption in blood and saline can be beneficial, because such laser light can be minimally invasive on surrounding tissue, which can reduce or eliminate damage to the tissue at or near the kidney stone. The laser can provide light having an output power that falls within a suitable range of output power, such as between 20 watts and 120 watts, between about 20 watts and about 120 watts, and others. These ranges of output power are mere examples, and other suitable output powers or ranges of output power can also be used. The optical fiber 128 can be a multi-mode fiber or a single-mode fiber.

A laser controller 132 (see FIG. 2) can be located on the grippable proximal portion 104 of the body 102. The laser controller 132 can toggle a state of the laser light between an operational state ("on") and a non-operational state ("off"). For example, the laser controller 132 can direct a wired and/or wireless signal to a laser that is located external to the nephroscope 100. The signal can turn on or turn off the laser. In some implementations, the practitioner can adjust one or more settings of the laser, such as the output power, on a housing of the laser. In some implementations, the practitioner can adjust one or more settings of the laser via the laser controller 132.

During a typical procedure, the practitioner can manipulate the laser controller 132 such that the laser can be operational for a period of time, such as one minutes, two minutes, three minutes, four minutes, or any suitable length of time. During the period of time of laser operation, the practitioner can manipulate the body 102 to move the delivered laser light across a surface of the kidney stone. The laser power level and the exposure times are such that the practitioner can safely switch the laser power on and off by hand, without a need for a mechanized or automated exposure mechanism. The laser power may also be low enough such that incidental exposure of surrounding tissue may not damage the tissue.

The practitioner can ablate the kidney stone by performing what is referred to as dusting of the surface of the kidney stone. Dusting can wear down the kidney stone in a controlled manner and can produce kidney stone particles that can be smaller than kidney stone fragments obtained from fragmenting or fracturing the kidney stone. For example, a typical kidney stone can be sized between about 1 mm and about 20 mm. Fragmenting or fracturing the kidney stone can produce kidney stone fragments that can be sized smaller than the size of the stone, such as between a few mm and less than about 10 mm in size. Dusting of the kidney stone can produce kidney stone particles that can be smaller than about 1 mm in size.

To remove the kidney stone fragments, the practitioner can use a stone retrieval device, such as a basket, that can pass through an orifice in the nephroscope 100. The practitioner can use the stone retrieval device to select and remove individual fragments. In addition to, or instead of, the stone retrieval device, the nephroscope 100 can include a flushing system to flush away the stone fragments.

The nephroscope 100 can include a flushing system at the distal end 110 of the body 102. The flushing system can controllably deliver a flow of an irrigation agent, such as a saline solution, to the ablation site and can controllably remove the irrigation agent and the kidney stone fragments from the ablation site.

The flushing system can include an irrigation lumen 134 (see FIG. 4) that extends along the body 102 to the distal end 110 of the body 102. The irrigation lumen 134 can deliver an irrigation fluid to the kidney stone and the kidney stone fragments. A proximal end of the irrigation lumen 134 can connect, via a suitable connector, to a suitable irrigation fluid source (e.g., a pump that can transport irrigation fluid from an irrigation fluid reservoir).

The flushing system can also include a suction lumen 136 (see FIG. 4) that extends along the body 102 to the distal end 110 of the body 102. The suction lumen 136 can remove the irrigation fluid and the kidney stone fragments from the kidney. A proximal end of the suction lumen 136 can connect, via a suitable connector, to a suitable suction or vacuum source that can suitably dispose of the irrigation agent and the kidney stone fragments.

The flushing system can include a flushing controller 138 (see FIG. 2) located on the grippable proximal portion 104 of the body 102. The flushing controller 138 can control a flow of irrigation fluid through the irrigation lumen 134 and suction in the suction lumen 136. The flushing controller 138 can include a depressible flushing control button that, when depressed repeatedly, cycles through one or more irrigation levels and/or suction levels, before turning off the irrigation and suction. For example, sequentially depressing the flushing control button can cause the irrigation and suction to switch from off to a lowest level, then from the lowest level to an intermediate level, then from the intermediate level to a highest level, then from the highest level to off, the from off to the lowest level, and so forth. The flushing controller 138 can control the irrigation and suction, together, with a single control. Other suitable flushing control elements can also be used, such as a positionable slide, a positionable lever, or a positionable dial that can specify an irrigation level and/or a suction level. The flushing controller 138 can select from one of a plurality of specified discrete irrigation/suction levels. The flushing controller 138 can specify the irrigation/suction level in a continuous (e.g., a non-discrete) manner.

The nephroscope 100 can optionally include a tube, chamber, additional working channel, or other passage 140 within a body of the nephroscope 100. A practitioner can use the passage 140 to deploy a separate tool or instrument, such as a lithotripter, a stone retrieval basket, or another suitable tool or instrument.

In some implementations, the entire nephroscope 100 can be disposed after a single use. In some implementations, one or more elements of the nephroscope 100 can be disposable, while one or more elements of the nephroscope 100 can be reused for later procedures. For example, the elongated rigid portion 106 and the flexible distal portion 108 can be detachable from (and/or reattachable to) the grippable proximal portion 104, so that the grippable proximal portion 104 can be cleaned and/or sterilized and reused, while the elongated rigid portion 106 and the flexible distal portion 108 can be discarded after a single use. As another example, the flexible distal portion 108 can be detachable from the elongated rigid portion 106, so that the grippable proximal portion 104 and the elongated rigid portion 106 can be cleaned and/or sterilized and reused, while the flexible distal portion 108 can be discarded after a single use.

Figure 7:
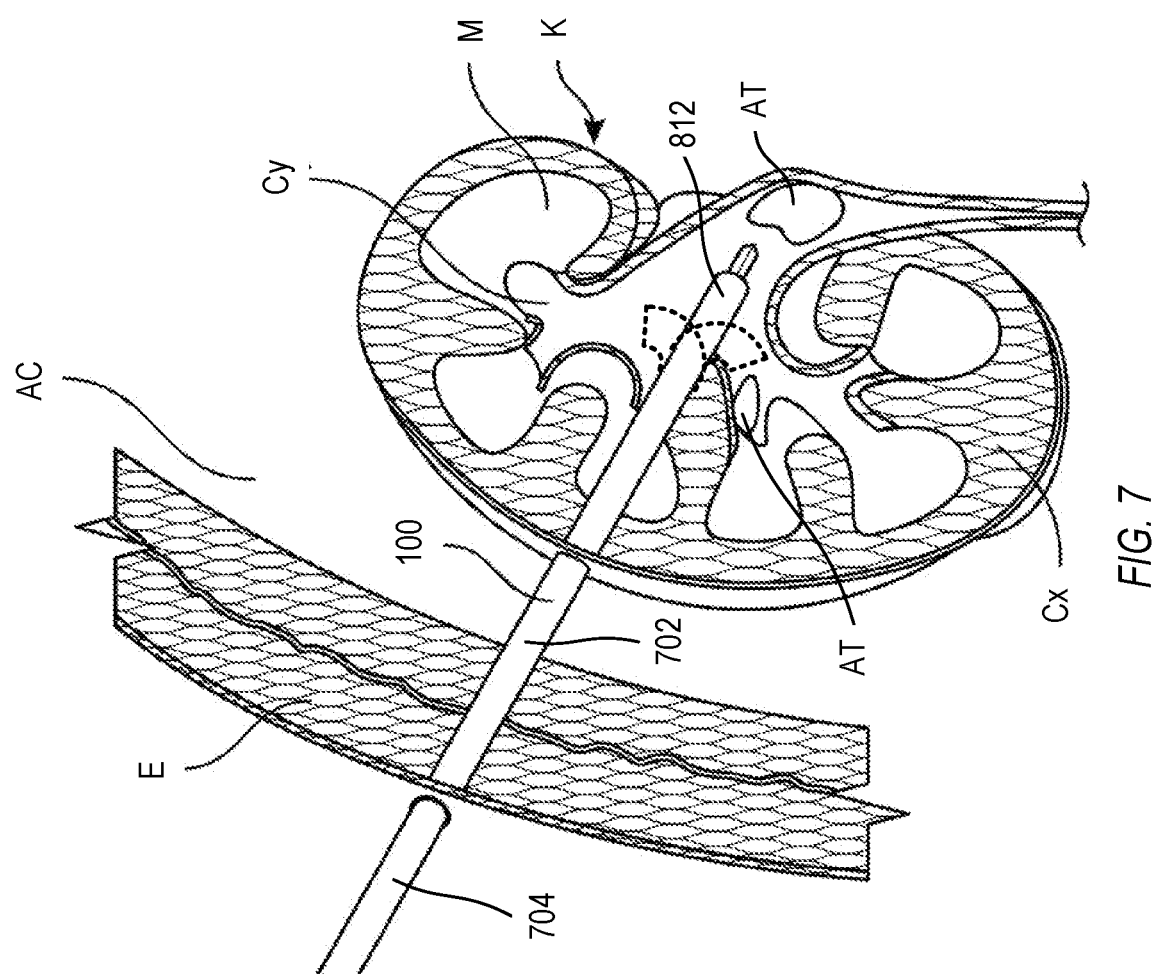
FIG. 7 is a schematic illustration of a kidney in an abdominal cavity, taken in a coronal plane.

FIG. 7 is a schematic illustration of kidney K in abdominal cavity AC taken in a coronal plane. Abdominal cavity AC can be defined by epidermal layers E that provide a barrier to access of kidney K. The nephroscope 100 can be inserted through epidermal layers E and into kidney K. Kidney K can comprise outer cortex Cx, medulla M and calyces Cy. Kidney stones can form in kidney K in various places, particularly in calyces Cy.

During use, the practitioner can insert the flexible distal portion 108 partially or fully into the body of the patient, and specifically into the kidney of the patient. During use, a distal portion 702 of the elongated rigid portion 106 can be located inside the body of the patient, while a proximal portion 704 of the elongated rigid portion 106 can remain outside the body of the patient. The grippable proximal portion 104 of the body 102 remains outside the patient's body before, during, and after use of the nephroscope 100. The grippable proximal portion 104 of the body 102 can be shaped to be grippable by a human hand.

Figure 8:
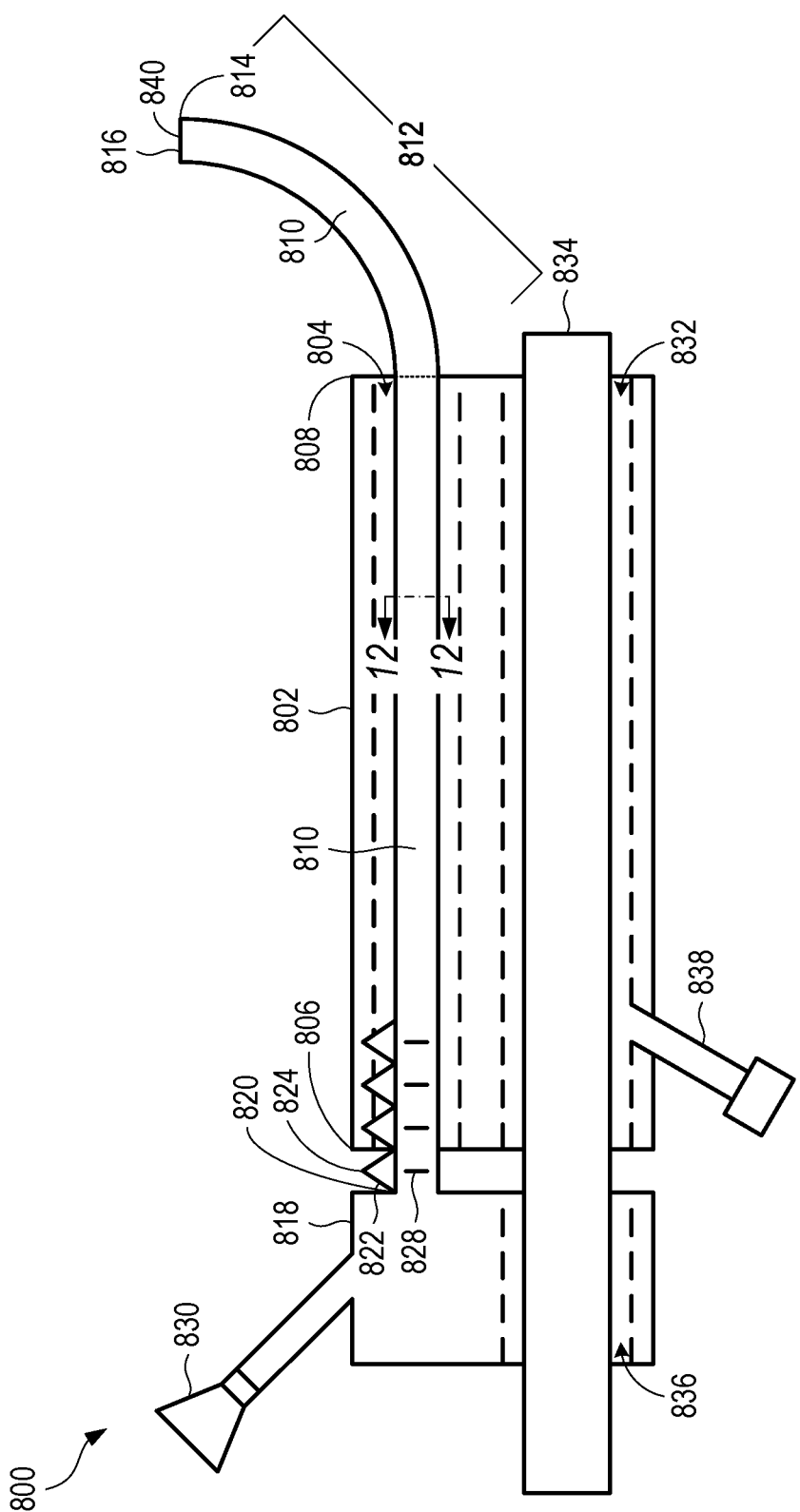
FIG. 8 shows a side view of an example of an endoscope.

FIG. 8 shows a side view of an example of an endoscope 800, such as a nephroscope. The endoscope 800 can include one or more moveable elements that, when moved with respect to each other, can vary a flexibility of the endoscope 800. For example, the moveable elements can control how much of a pre-biased (or curved) element extends from a rigid element. When the pre-biased element is fully extended, the endoscope 800 can have a maximum flexibility. When the pre-biased element is fully retracted, the endoscope 800 can have a minimum flexibility. When the pre-biased element is partially retracted, the endoscope 800 can have an intermediate flexibility. Such variable flexibility can allow a practitioner to use a single endoscope 800 to perform different functions. For example, setting the endoscope 800 to a minimum flexibility (e.g. to a rigid or near-rigid position) can allow the endoscope 800 to operate with a rigid lithotripter and a flexible lithotripter, such as a laser lithotripter. Setting the endoscope 800 to a flexibility that is more flexible than the minimum flexibility can allow the endoscope 800 to perform laser lithotripsy, retrieval, or visualization functions. These functions are merely examples; the endoscope 800 can also perform other suitable functions with varying degrees of flexibility. Examples of the moveable elements are described in detail below, with regard to FIGS. 8-12.

Figure 10:
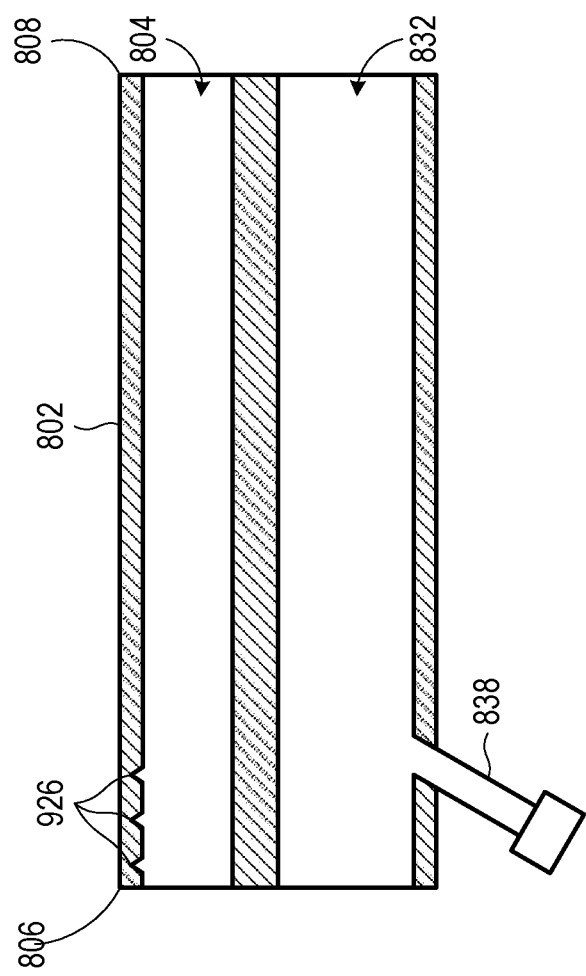
FIG. 10 shows a cross-sectional side view of the elongate body of FIG. 8.

A substantially rigid elongate body 802 can be at least partially insertable into a kidney of a patient. The elongate body 802 can be formed from one or more suitable biocompatible materials, such as plastic, metal, or others. FIG. 10 shows a cross-sectional side view of the elongate body 802 of FIG. 8.

The elongate body 802 can include a visualization channel 804 that can extend through the elongate body 802 from a proximal end 806 of the elongate body 802 to a distal end 808 of the elongate body 802. The visualization channel 804, or telescope channel, can accommodate one or more visualization instruments, such as a telescope or "scope." The visualization channel 804 can be substantially straight, such that a cross-section of the visualization channel 804, taken in a plane that is substantially orthogonal to the visualization channel 804, remains substantially constant at each location between the proximal end 806 of the elongate body 802 and the distal end 808 of the elongate body 802. The visualization channel 804 can include one or more bends. The visualization channel 804 can have a substantially circular cross-section, taken in a plane that is substantially orthogonal to the visualization channel 804.

An elongate viewing instrument 810, such as a telescope or endoscope, can be advanced distally and retracted proximally through the visualization channel 804 of the elongate body 802. The telescope or endoscope can include one or more lenses, mirrors, and/or optical fibers, and can be disposed in an optical passageway 1202 (FIG. 12) that extends along a length of the elongate viewing instrument 810. The elongate viewing instrument 810 can be formed as an elongate tube or other suitable shape. The elongate viewing instrument 810 can extend distally beyond the distal end 808 of the elongate body 802 such as when the elongate viewing instrument 810 is fully advanced distally.

The elongate viewing instrument 810 can include a distal portion 812 that is pre-biased such as to assume a bent or curved shape when the distal portion 812 is unconfined, such that the distal portion 812 of the elongate viewing instrument 810 can bend or curve when the distal portion 812 of the elongate viewing instrument 810 is advanced distally to exit the visualization channel 804 and can generally straighten when the distal portion 812 of the elongate viewing instrument 810 is retracted proximally to enter into the visualization channel 804.

Using such a pre-biased distal portion 812 can provide additional flexibility for a practitioner in examining regions of a kidney or other suitable target. For example, FIG. 7 shows an example where a practitioner has inserted the device through a single access point (e.g., a puncture hole through which the endoscope or nephroscope is inserted). During a procedure, a practitioner can move the distal portion 812 as needed to examine other areas of the kidney or other target, without withdrawing the device from the access point. For example, a practitioner can move the distal portion 812 to search for an ablation target (AT), and/or move from one ablation target to another. The practitioner can move the distal portion 812 without moving the rigid portion of the elongate viewing instrument 810, as shown in FIG. 7.

A distal end 814 of the elongate viewing instrument 810 can further include a light port 816 that can illuminate a target and provide an image of the illuminated target. For example, the target can be a kidney stone. Other diagnostics and/or therapies can be used, which can search for and/or treat other suitable targets. For example, a practitioner can visualize a tumor, and can use an access port to perform a biopsy.

The elongate viewing instrument 810 can further include a fiber 840 that can perform one or more functions. For example, the fiber 840 can deliver laser light to the distal end 814 of the elongate viewing instrument 810 to ablate the target. As another example, the fiber 840 can be a diagnostic fiber. Such a diagnostic fiber can deliver light to the target. Such a diagnostic fiber can send image signals back to the video processor for viewing Such a diagnostic fiber can send image signals to a main viewing element, for example, an additional renal calyx to see if any residual stones remain after a procedure has been performed.

Figure 12:
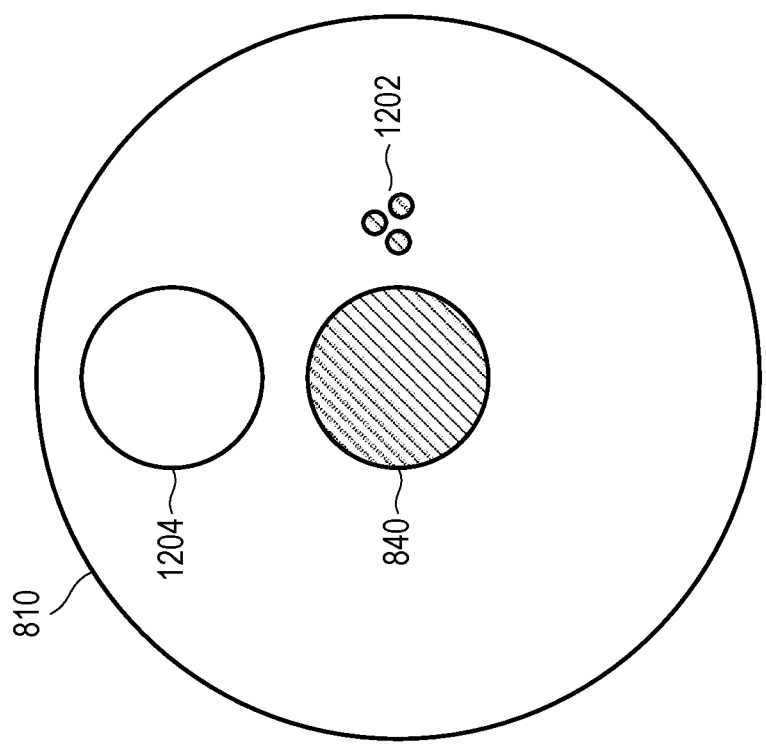
FIG. 12 shows a cross-sectional view of the elongate viewing instrument of the endoscope of FIG. 8.

FIG. 12 shows a cross-sectional view of the elongate viewing instrument 810 of the endoscope of FIG. 8. The cross-section of FIG. 12 shows the fiber 840, which can perform diagnostic and/or ablative functions.

One or more wires 1202 can extend along a length of the elongate viewing instrument 810. The one or more wires 1202 can electrically power an illuminator at the distal end of the elongate viewing instrument 810, such as a white-light light-emitting diode, which can illuminate the target. The one or more wires 1202 can electrically power a camera at the distal end of the elongate viewing instrument 810, which can capture an image of the target. The one or more wires 1202 can deliver an analog and/or digital signal from the camera, such as to a display electrical port and/or a display.

The elongate viewing instrument 810 can include an optical passageway 1204, which can accommodate one or more lenses, mirrors, fibers, and/or other suitable optical components, which can form an image of the target (in an analog manner) at an eyepiece or viewing port.

Continuing with FIG. 8, a moveable actuator 818 can be coupled to a proximal end 820 of the elongate viewing instrument 810 and can be located at or near the proximal end 806 of the elongate body 802. The moveable actuator 818 can be advanceable distally toward the elongate body 802 to, in response, distally advance the elongate viewing instrument 810, and can be retractable proximally away from the elongate body 802 to, in response, proximally retract the elongate viewing instrument 810. Such advancement and/or retraction can be performed via a trigger, a lever, a slide, or other suitable actuator mechanism.

The elongate body 802 and the moveable actuator 818 can be grippable, such that forcing the elongate body 802 and the moveable actuator 818 toward each other can, in response, distally advance the elongate viewing instrument 810 and pulling apart the elongate body 802 and the moveable actuator 818 proximally can, in response, retract the elongate viewing instrument 810. The elongate body 802 and the moveable actuator 818 can each include a respective handle (not shown), which can be gripped to force the elongate body 802 and the moveable actuator 818 toward each other and gripped to pull apart the elongate body 802 and the moveable actuator 818.

The elongate body 802 and the moveable actuator 818 can include indexing or positioning elements 822 such as can position the moveable actuator 818 at one of a plurality of specified or indexed positions, relative to the elongate body 802. The positioning elements 822 can removably snap the moveable actuator 818 to one of the plurality of specified positions, relative to the elongate body 802. For example, one or more indentations can couple with one or more corresponding protrusions or mechanical stops such as to snap the elongate body 802 and the moveable actuator 818 to establish or provide a desired one of a number of indexed specified separation values.

The positioning elements 822 can be located at a proximal portion of the elongate viewing instrument 810 and a proximal portion of the visualization channel 804. The positioning elements 822 can be located at any suitable location or locations at or between the proximal portions and distal portions of the elongate viewing instrument 810 and the visualization channel 804.

The positioning elements 822 can include at least one protrusion 824 on the elongate viewing instrument 810 such as can removably engage at least one indentation 926 (FIG. 9) in the visualization channel 804.

Figure 11:
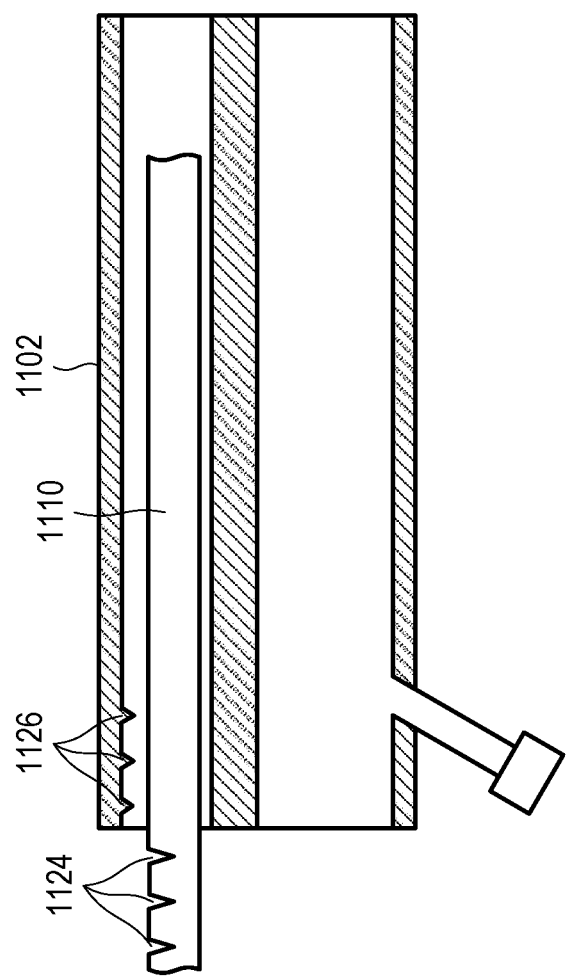
FIG. 11 shows a cross-sectional side view of an example of an elongate body and corresponding elongate viewing instrument.

Similarly, FIG. 11 shows a cross-sectional side view of an example of an elongate body 1102 and corresponding elongate viewing instrument 1110. The visualization channel through the elongate body 1102 can include at least one protrusion 1126 that can extend from a wall of the visualization channel into the visualization channel. The elongate viewing instrument 1110 can include at least one indentation 1124 on the elongate viewing instrument 1110.

The positioning elements 822 can be equally spaced or substantially equally spaced. For example, the positioning elements 822 can be spaced apart by 1 mm, such that the plurality of specified or indexed positions are also spaced apart by 1 mm. This equal or substantially equal spacing can allow a practitioner to move the elongate viewing instrument 810 to a desired location to within 1 mm. Other numerical values can also be used.

The positioning elements 822 can be unequally spaced. For example, the positioning elements 822 can be spaced apart with a spacing that can vary from element to element, such as a change in the flexibility of the elongate viewing instrument 810 can vary in equal increments from element to element. Other suitable spacings can also be used.

Returning to FIG. 8, the elongate viewing instrument 810 can include visually observable indicia 828 that can be located at a proximal portion of the elongate viewing instrument 810. The visually observable indicia 828 can provide an index or can otherwise indicate a length of the distal portion 812 of the elongate viewing instrument 810 that extends distally beyond a distal end of the visualization channel 804. For example, the visually observable indicia 828 can include ruled markings corresponding to length, such as at a regularly spaced interval, such as in mm. The visually observable indicia 828 can optionally include numerical values that can indicate the length of the distal portion 812 of the elongate viewing instrument 810 that extends distally beyond a distal end of the visualization channel 804. Other suitable visually observable indicia 828 can also be used.

A viewing element 830 can be coupled to the moveable actuator 818 and can provide an image of the illuminated target. For example, during use, a practitioner can observe the viewing element 830 to view the illuminated target, such as a kidney stone, to determine a suitable location for an instrument to affect the illuminated target, such as for a lithotripter that can ablate or otherwise break up a kidney stone. The elongate viewing instrument 810 can include a telescope that can form the image of the illuminated target, with the viewing element 830 including a viewing port, such as an eyepiece, coupled to the telescope to provide the image of the illuminated target. The light port 816 of the elongate viewing instrument 810 can include a camera that can form the image of the illuminated target, with the viewing element 830 including an electrical port that is electrically coupled to the camera and can connect to a video monitor to display the image of the illuminated target. The light port 816 of the elongate viewing instrument 810 can include a camera that can form the image of the illuminated target, with the viewing element 830 including a video monitor that is electrically coupled to the camera and can display the image of the illuminated target.

The elongate body 802 can further include an elongate body lithotripter channel 832 or other working channel such as can be sized to accommodate a lithotripter 834. The elongate body lithotripter channel 832 can extend through the elongate body 802 from the proximal end 806 of the elongate body 802 to the distal end 808 of the elongate body 802. The elongate body lithotripter channel 832 can be substantially parallel to the visualization channel 804 or can be angled at a suitable angle with respect to the visualization channel 804. The elongate body lithotripter channel 832 can be substantially straight, such that a cross-section of the elongate body lithotripter channel 832, taken in a plane that is substantially orthogonal to the elongate body lithotripter channel 832, remains substantially constant at each location between the proximal end 806 of the elongate body 802 and the distal end 808 of the elongate body 802. The elongate body lithotripter channel 832 can have a substantially circular cross-section, taken in a plane that is substantially orthogonal to the elongate body lithotripter channel 832.

The moveable actuator 818 can include a moveable actuator lithotripter channel 836 or other working channel such as can be sized to accommodate the lithotripter 834. The moveable actuator lithotripter channel 836 can extend through the moveable actuator 818 from a proximal end of the moveable actuator 818 to a distal end of the moveable actuator 818. The moveable actuator lithotripter channel 836 can be substantially coaxial with the elongate body lithotripter channel 832. The moveable actuator lithotripter channel 836 can include one or more seals that can help prevent irrigation fluid, which can be pressurized, from passing through the moveable actuator lithotripter channel 836 and potentially damaging one or more components and/or leaking out of the device. One or more seals can surround one or more wires and/or electrical connectors. One or more seals can be located at a proximal end of the moveable actuator lithotripter channel 836 and/or a distal end of the moveable actuator lithotripter channel 836.

The elongate body 802 can further include an irrigation fluid port 838 that can extend to the elongate body lithotripter channel 832 through a wall of the elongate body 802. The irrigation fluid port 838 and the visualization channel 804 can be disposed on opposite sides of the elongate body lithotripter channel 832. The irrigation fluid port 838 can include one or more seals that can help prevent irrigation fluid, which can be pressurized, from passing through the irrigation fluid port 838 and potentially damaging one or more components and/or leaking out of the device. One or more seals can surround one or more wires and/or electrical connectors. One or more seals can be located at a proximal end of the irrigation fluid port 838 and/or a distal end of the irrigation fluid port 838.

During use, a practitioner can adjust how much of the viewing instrument 810 extends distally beyond the distal end 808 of the elongate body 802 such as by forcing together or pulling apart the elongate body 802 and the moveable actuator 818 (e.g., advancing the moveable actuator 818 toward the elongate body 802 or retracting the moveable actuator 818 away from the elongate body 802). In the configuration of FIG. 8, a practitioner has fully forced the elongate body 802 and the moveable actuator 818 together, such that the elongate viewing instrument 810 is fully advanced distally.

Figure 9:
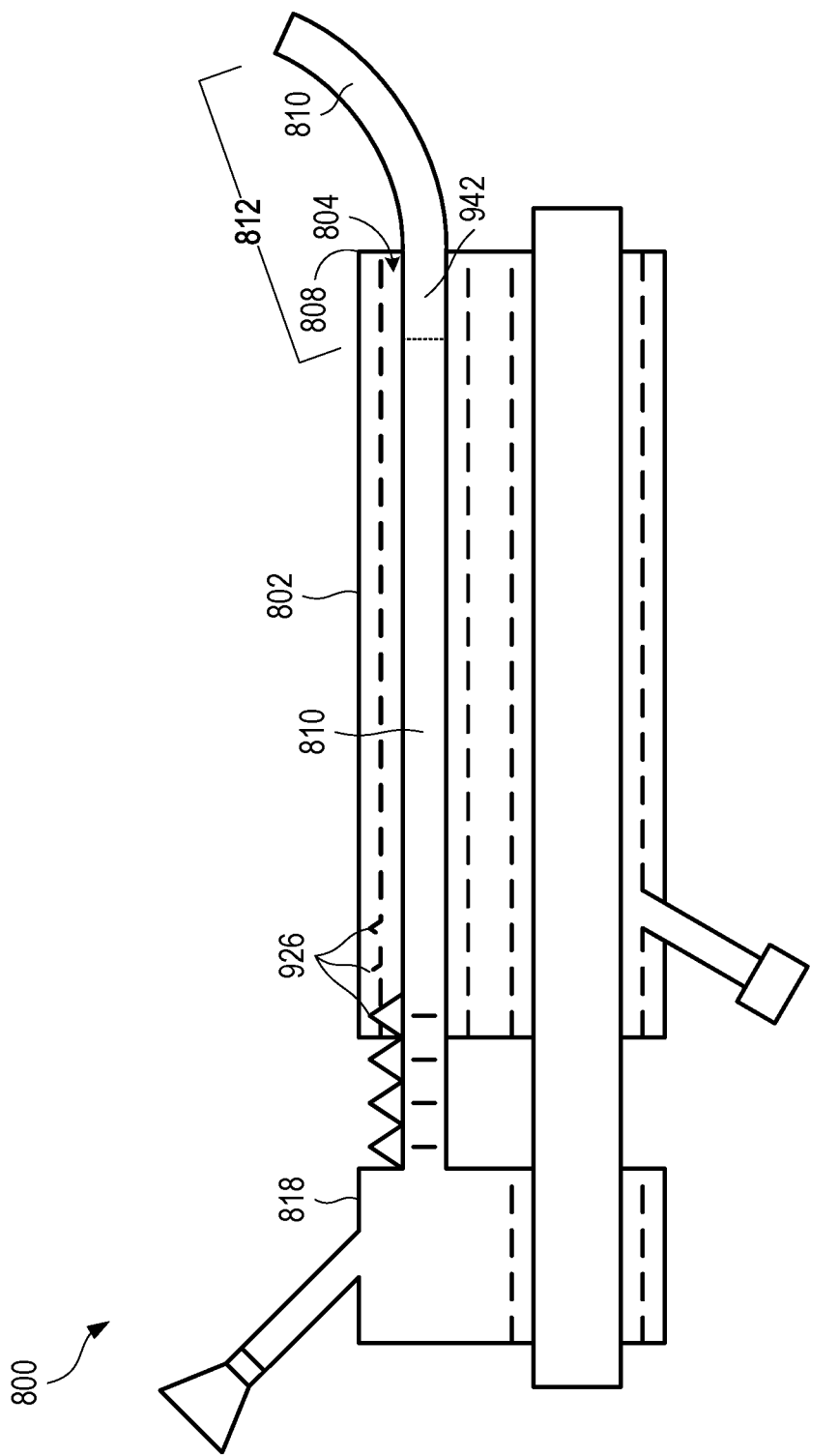
FIG. 9 shows the insertable endoscope of FIG. 8, with a portion of the distal portion of the elongate viewing instrument being retracted proximally into the visualization channel.

FIG. 9 shows the insertable endoscope 800 of FIG. 8, with a portion 942 of the distal portion 812 of the elongate viewing instrument 810 being retracted proximally into the visualization channel 804. Because the distal portion 812 can be pre-biased to bend or curve, varying the length of the distal portion 812 that extends distally beyond the distal end 808 of the elongate body 802 can in turn vary the orientation at which the endoscope 800 can observe the target.

The pre-biasing can cause the distal portion 812 to curve in a suitable direction. For example, the pre-biasing can cause to curve radially away from a longitudinal axis of the visualization channel 804, so that as the distal portion 812 is advanced and/or retracted during use, the distal portion 812 can remain in a plane that includes the longitudinal axis of the visualization channel 804. Other suitable curving schemes can also be used.

Figure 13:
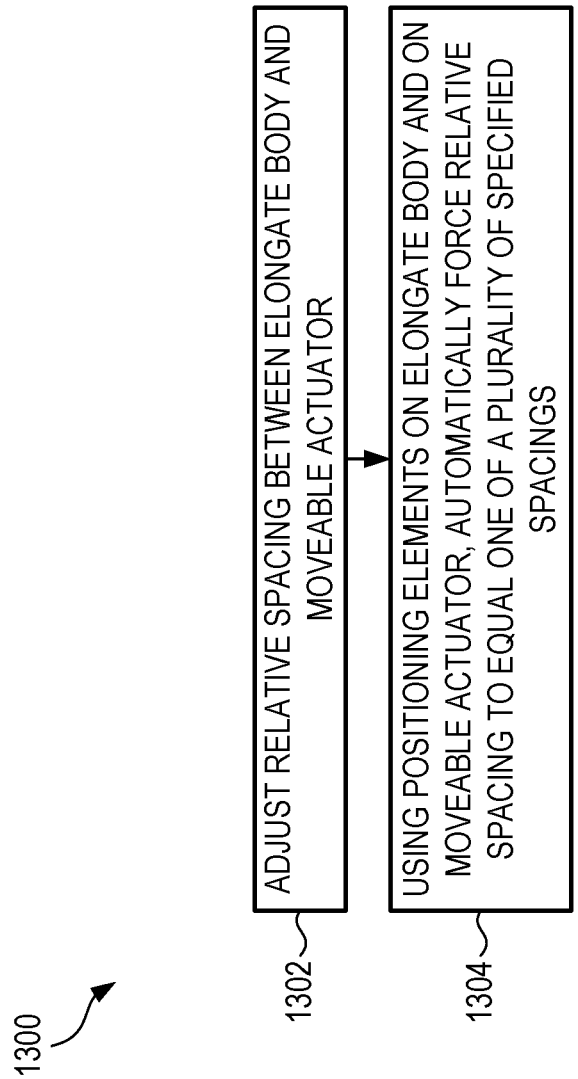
FIG. 13 shows an example of a method for adjusting an endoscope.

FIG. 13 shows an example of a method 1200 for adjusting an endoscope, such as the endoscope 800 of FIG. 8. The method 1300 is but one example of a method for adjusting an endoscope; other methods can also be used.

At operation 1302, a relative spacing between an elongate body and a moveable actuator can be adjusted. The moveable actuator can include an elongate viewing instrument that can extend distally from the moveable actuator. The elongate viewing instrument can extend through a visualization channel in the elongate body and can extend distally beyond a distal end of the elongate body such that adjusting the relative spacing adjusts how much of the elongate viewing instrument extends distally beyond the distal end of the elongate body. The elongate viewing instrument can include a distal portion that is pre-biased to assume a curved shape when the distal portion is unconfined, such that the distal portion of the elongate viewing instrument can curve when the distal portion of the elongate viewing instrument is advanced distally to exit the visualization channel and can generally straighten when the distal portion of the elongate viewing instrument is retracted proximally to enter the visualization channel.

At operation 1304, using positioning elements on the elongate body and the moveable actuator, the relative spacing can be automatically forced to equal one of a plurality of specified spacings, such as can be represented by corresponding indicia that can be visually observable to the user, if desired. For example, if the positioning elements are spaced apart by 1 mm, the relative spacing can be automatically forced to equal one of a specified value, the specified value plus 1 mm, the specified value minus 1 mm, the specified value plus 2 mm, the specified value minus 2 mm, and so forth.

The automatic forcing can use one or more positioning elements on the elongate body that engage one or more corresponding positioning elements on the moveable actuator. The positioning elements can include at least one protrusion on the elongate viewing instrument that can removably engage at least one indentation in the visualization channel. The positioning elements can include at least one protrusion in the visualization channel that can removably engage at least one indentation on the elongate viewing instrument. Traversing such protrusions or other positioning elements can provide the user with haptic feedback about the act or degree of extension or retraction.

FIG. 14 shows an example of a method for imaging using an endoscope. The method 1400 can be executed on the endoscope 800 of FIGS. 8-11, or any other suitable endoscope. The method 1400 is but one example of a method for imaging using an endoscope. Other suitable methods can also be used.

At operation 1402, a practitioner can use the endoscope to illuminate, with a distal end of the endoscope, an area proximate the distal end of the endoscope.

At operation 1404, the practitioner can use the endoscope to selectively articulate a flexible distal portion of the endoscope to adjust a position of the distal end of the endoscope to locate a first target.

At operation 1406, the practitioner can use the endoscope to identify, from an image of the illuminated area when the distal end of the endoscope is at a first position, the first target in the area proximate the distal end of the endoscope.

At operation 1408, the practitioner can use the endoscope to lock articulation of the flexible distal portion of the endoscope to fixedly position the distal end of the endoscope at the first position.

At optional operation 1410, the practitioner can use the endoscope to unlock the articulation of the flexible distal portion of the endoscope.

At optional operation 1412, the practitioner can use the endoscope to selectively articulate the flexible distal portion of the endoscope to adjust a position of the distal end of the endoscope to locate a second target.

At optional operation 1414, the practitioner can use the endoscope to identify, from an image of the illuminated area when the distal end of the endoscope is at a second position, the second target in the area proximate the distal end of the endoscope.

In addition to being executable on an endoscope, the method 1400 can also be executed on a nephroscope, such as the nephroscope 100 of FIGS. 1-5, or on other suitable nephroscopes.

EXAMPLES

To further illustrate the device, related system, and/or related method discussed herein, a non-limiting list of examples is provided below. Each of the following non-limiting examples can stand on its own or can be combined in any permutation or combination with any one or more of the other examples.

In Example 1, an endoscope can include: a substantially rigid elongate body at least partially insertable into a kidney of a patient, the elongate body including a visualization channel that extends through the elongate body from a proximal end of the elongate body to a distal end of the elongate body; and an elongate viewing instrument configured to advance distally and retract proximally through the visualization channel of the elongate body, the elongate viewing instrument extending distally beyond the distal end of the elongate body when the elongate viewing instrument is fully advanced distally, the elongate viewing instrument including a distal portion that is pre-biased to assume a curved shape when the distal portion is unconfined, such that the distal portion of the elongate viewing instrument is configured to curve when the distal portion of the elongate viewing instrument is advanced distally to exit the visualization channel and configured to generally straighten when the distal portion of the elongate viewing instrument is retracted proximally to enter the visualization channel, a distal end of the elongate viewing instrument further including a light port that is configured to illuminate a target and provide an image of the illuminated target.

In Example 2, the endoscope of Example 1 can optionally further include a moveable actuator coupled to a proximal end of the elongate viewing instrument and located proximal to the proximal end of the elongate body, the moveable actuator being advanceable distally toward the elongate body to distally advance the elongate viewing instrument and retractable proximally away from the elongate body to proximally retract the elongate viewing instrument.

In Example 3, the endoscope of any one of Examples 1-2 can optionally be configured such that the elongate body and the moveable actuator are grippable, such that forcing the elongate body and the moveable actuator toward each other distally advances the elongate viewing instrument and pulling apart the elongate body and the moveable actuator proximally retracts the elongate viewing instrument.

In Example 4, the endoscope of any one of Examples 1-3 can optionally be configured such that the elongate body and the moveable actuator include positioning elements configured to position the moveable actuator at one of a plurality of specified positions, relative to the elongate body.

In Example 5, the endoscope of any one of Examples 1-4 can optionally be configured such that the positioning elements are configured to removably snap the moveable actuator to one of the plurality of specified positions, relative to the elongate body.

In Example 6, the endoscope of any one of Examples 1-5 can optionally be configured such that the positioning elements are located at a proximal portion of the elongate viewing instrument and a proximal portion of the visualization channel.

In Example 7, the endoscope of any one of Examples 1-6 can optionally be configured such that the positioning elements include at least one protrusion on the elongate viewing instrument configured to removably engage at least one indentation in the visualization channel.

In Example 8, the endoscope of any one of Examples 1-7 can optionally be configured such that the positioning elements include at least one protrusion in the visualization channel configured to removably engage at least one indentation on the elongate viewing instrument.

In Example 9, the endoscope of any one of Examples 1-8 can optionally further include visually observable indicia that are located at a proximal portion of the elongate viewing instrument, the visually observable indicia configured to indicate a length of the distal portion of the elongate viewing instrument that extends distally beyond a distal end of the visualization channel.

In Example 10, the endoscope of any one of Examples 1-9 can optionally be configured such that the elongate viewing instrument includes a telescope that is coupled to the moveable actuator, the telescope being disposed in an optical passageway and configured to form an image of the illuminated target; and further comprising a viewing port coupled to the telescope to provide the image of the illuminated target.

In Example 11, the endoscope of any one of Examples 1-10 can optionally be configured such that the light port of the elongate viewing instrument includes a camera configured to capture an image of the illuminated target; and further comprising an electrical port that is electrically coupled to the camera and configured to connect to a video monitor to display the image of the illuminated target.

In Example 12, the endoscope of any one of Examples 1-11 can optionally be configured such that the light port of the elongate viewing instrument includes a camera configured to capture an image of the illuminated target; and further comprising a video monitor that is electrically coupled to the camera and configured to display the image of the illuminated target.

In Example 13, the endoscope of any one of Examples 1-12 can optionally be configured such that: the elongate body further includes an elongate body lithotripter channel that is sized to accommodate a lithotripter and extends through the elongate body from the proximal end of the elongate body to the distal end of the elongate body, the elongate body lithotripter channel being substantially parallel to the visualization channel; and the moveable actuator includes a moveable actuator lithotripter channel that is sized to accommodate a lithotripter and extends through the moveable actuator from a proximal end of the moveable actuator to a distal end of the moveable actuator, the moveable actuator lithotripter channel being substantially coaxial with the elongate body lithotripter channel.

In Example 14, the endoscope of any one of Examples 1-13 can optionally be configured such that the elongate body further includes an irrigation fluid port that extends to the elongate body lithotripter channel through a wall of the elongate body, the irrigation fluid port and the visualization channel being disposed on opposite sides of the elongate body lithotripter channel.

In Example 15, the endoscope of any one of Examples 1-14 can optionally be configured such that the elongate body lithotripter channel is configured to allow a rigid lithotripter and an optical fiber to pass through the elongate body lithotripter channel.

In Example 16, the endoscope of any one of Examples 1-15 can optionally be configured such that the elongate viewing instrument further includes a fiber configured to deliver laser light to the distal end of the elongate viewing instrument to ablate the target.

In Example 17, a method for adjusting an endoscope can include: adjusting a relative spacing between an elongate body and a moveable actuator, the moveable actuator including an elongate viewing instrument that extends distally from the moveable actuator, the elongate viewing instrument extending through a visualization channel in the elongate body and extending distally beyond a distal end of the elongate body such that adjusting the relative spacing adjusts how much of the elongate viewing instrument extends distally beyond the distal end of the elongate body, the elongate viewing instrument including a distal portion that is pre-biased to assume a curved shape when the distal portion is unconfined, such that the distal portion of the elongate viewing instrument is configured to curve when the distal portion of the elongate viewing instrument is advanced distally to exit the visualization channel and configured to generally straighten when the distal portion of the elongate viewing instrument is retracted proximally to enter the visualization channel; and automatically forcing, using one or more positioning elements on the elongate body that engage one or more corresponding positioning elements on the moveable actuator, the relative spacing to equal one of a plurality of specified spacings.

In Example 18, the method of Example 17 can optionally be configured such that the one or more positioning elements include at least one protrusion on the elongate viewing instrument configured to removably engage at least one indentation in the visualization channel.

In Example 19, the method of any one of Examples 17-18 can optionally be configured such that the one or more positioning elements include at least one protrusion in the visualization channel configured to removably engage at least one indentation on the elongate viewing instrument.

In Example 20, an endoscope can include: an elongate body; a moveable actuator coupled to the elongate body, the moveable actuator being moveable to adjust a relative spacing between the moveable actuator and the elongate body; an elongate viewing instrument that extends distally from the moveable actuator, the elongate viewing instrument extending through a visualization channel in the elongate body and extending distally beyond a distal end of the elongate body such that adjusting the relative spacing adjusts how much of the elongate viewing instrument extends distally beyond the distal end of the elongate body, the elongate viewing instrument including a distal portion that is pre-biased to assume a curved shape when the distal portion is unconfined such that the distal portion of the elongate viewing instrument is configured to curve when the distal portion of the elongate viewing instrument is advanced distally to exit the visualization channel and configured to generally straighten when the distal portion of the elongate viewing instrument is retracted proximally to enter the visualization channel; and positioning elements on the elongate body and the moveable actuator, the positioning elements configured to snap the relative spacing between the moveable actuator and the elongate body to equal one of a plurality of specified spacings.

What is claimed is:

1. An endoscope, comprising:
   a substantially rigid elongate body at least partially insertable into a kidney of a patient,
   the elongate body including a visualization channel that extends through the elongate body from a proximal end of the elongate body to a distal end of the elongate body;
   an elongate viewing instrument configured to advance distally and retract proximally through the visualization channel of the elongate body, and
   a moveable actuator coupled to a proximal end of the elongate viewing instrument and located proximal to the proximal end of the elongate body, the moveable actuator being advanceable distally toward the elongate body to distally advance the elongate viewing instrument and retractable proximally away from the elongate body to proximally retract the elongate viewing instrument,
   the elongate viewing instrument extending distally beyond the distal end of the elongate body when the elongate viewing instrument is fully advanced distally,
   the elongate viewing instrument including a distal portion that extends beyond the distal end of the elongate body to a distalmost end of the elongate viewing instrument,
   the distal portion being entirely pre-biased to assume a generally circular curved shape when the distal portion is unconfined, such that the distal portion of the elongate viewing instrument is configured to curve when the distal portion of the elongate viewing instrument is advanced distally to exit the visualization channel and configured to generally straighten when the distal portion of the elongate viewing instrument is retracted proximally to enter the visualization channel,
   a distal end of the elongate viewing instrument further including a light port that is configured to illuminate a target and provide an image of the illuminated target.

2. The endoscope of claim 1, wherein the elongate body and the moveable actuator are grippable, such that forcing the elongate body and the moveable actuator toward each other distally advances the elongate viewing instrument and pulling apart the elongate body and the moveable actuator proximally retracts the elongate viewing instrument.

3. The endoscope of claim 1, wherein the elongate body and the moveable actuator include positioning elements configured to position the moveable actuator at one of a plurality of specified positions, relative to the elongate body, the positioning elements including at least one protrusion configured to removably engage at least one indentation.

4. The endoscope of claim 3, wherein the positioning elements are configured to removably snap the moveable actuator to one of the plurality of specified positions, relative to the elongate body.

5. The endoscope of claim 3, wherein the positioning elements are located at a proximal portion of the elongate viewing instrument and a proximal portion of the visualization channel.

6. The endoscope of claim 3, wherein the positioning elements include at least one protrusion on the elongate viewing instrument configured to removably engage at least one indentation in the visualization channel.

7. The endoscope of claim 3, wherein the positioning elements include at least one protrusion in the visualization channel configured to removably engage at least one indentation on the elongate viewing instrument.

8. The endoscope of claim 3, further comprising visually observable indicia that are located at a proximal portion of the elongate viewing instrument, the visually observable indicia configured to indicate a length of the distal portion of the elongate viewing instrument that extends distally beyond a distal end of the visualization channel.

9. The endoscope of claim 1, wherein:
   the elongate viewing instrument includes a telescope that is coupled to the moveable actuator, the telescope being disposed in an optical passageway and configured to form an image of the illuminated target; and
   the endoscope further comprises a viewing port coupled to the telescope to provide the image of the illuminated target.

10. The endoscope of claim 1, wherein:
    the light port of the elongate viewing instrument includes a camera configured to capture an image of the illuminated target; and
    the endoscope further comprises an electrical port that is electrically coupled to the camera and configured to connect to a video monitor to display the image of the illuminated target.

11. The endoscope of claim 1, wherein:
    the light port of the elongate viewing instrument includes a camera configured to capture an image of the illuminated target; and
    the endoscope further comprises a video monitor that is electrically coupled to the camera and configured to display the image of the illuminated target.

12. The endoscope of claim 1, wherein:
    the elongate body further includes an elongate body lithotripter channel that is sized to accommodate a lithotripter and extends through the elongate body from the proximal end of the elongate body to the distal end of the elongate body, the elongate body lithotripter channel being substantially parallel to the visualization channel; and
    the moveable actuator includes a moveable actuator lithotripter channel that is sized to accommodate a lithotripter and extends through the moveable actuator from a proximal end of the moveable actuator to a distal end of the moveable actuator, the moveable actuator lithotripter channel being substantially coaxial with the elongate body lithotripter channel.

13. The endoscope of claim 12, wherein the elongate body further includes an irrigation fluid port that extends to the elongate body lithotripter channel through a wall of the elongate body, the irrigation fluid port and the visualization channel being disposed on opposite sides of the elongate body lithotripter channel.

14. The endoscope of claim 13, wherein the elongate body lithotripter channel is configured to allow a rigid lithotripter and an optical fiber to pass through the elongate body lithotripter channel.

15. The endoscope of claim 1, wherein the elongate viewing instrument further includes a fiber configured to deliver laser light to the distal end of the elongate viewing instrument to ablate the target.

16. A method for adjusting an endoscope, the method comprising:
    adjusting a relative spacing between an elongate body and a moveable actuator, the moveable actuator including an elongate viewing instrument that extends distally from the moveable actuator, the elongate viewing instrument extending through a visualization channel in the elongate body and extending distally beyond a distal end of the elongate body such that adjusting the relative spacing adjusts how much of the elongate viewing instrument extends distally beyond the distal end of the elongate body, the elongate viewing instrument including a distal portion that extends beyond the distal end of the elongate body to a distalmost end of the elongate viewing instrument, the distal portion being entirely pre-biased to assume a generally circular curved shape when the distal portion is unconfined, such that the distal portion of the elongate viewing instrument is configured to curve when the distal portion of the elongate viewing instrument is advanced distally to exit the visualization channel and configured to generally straighten when the distal portion of the elongate viewing instrument is retracted proximally to enter the visualization channel; and
    automatically forcing, using one or more positioning elements on the elongate body that engage one or more corresponding positioning elements on the moveable actuator, the relative spacing to equal one of a plurality of specified spacings.

17. The method of claim 16, wherein the one or more positioning elements include at least one protrusion on the elongate viewing instrument configured to removably engage at least one indentation in the visualization channel.

18. The method of claim 16, wherein the one or more positioning elements include at least one protrusion in the visualization channel configured to removably engage at least one indentation on the elongate viewing instrument.

19. An endoscope, comprising:
    an elongate body;
    a moveable actuator coupled to the elongate body, the moveable actuator being moveable to adjust a relative spacing between the moveable actuator and the elongate body;
    an elongate viewing instrument that extends distally from the moveable actuator, the elongate viewing instrument extending through a visualization channel in the elongate body and extending distally beyond a distal end of the elongate body such that adjusting the relative spacing adjusts how much of the elongate viewing instrument extends distally beyond the distal end of the elongate body, the elongate viewing instrument including a distal portion that extends beyond the distal end of the elongate body to a distalmost end of the elongate viewing instrument, the distal portion being entirely pre-biased to assume a generally circular curved shape when the distal portion is unconfined such that the distal portion of the elongate viewing instrument is configured to curve when the distal portion of the elongate viewing instrument is advanced distally to exit the visualization channel and configured to generally straighten when the distal portion of the elongate viewing instrument is retracted proximally to enter the visualization channel; and
    positioning elements on the elongate body and the moveable actuator, the positioning elements configured to snap the relative spacing between the moveable actuator and the elongate body to equal one of a plurality of specified spacings.

\* \* \* \* \*